US009055908B2

(12) United States Patent
Wackym et al.

(10) Patent No.: US 9,055,908 B2
(45) Date of Patent: Jun. 16, 2015

(54) SYSTEMS AND METHODS FOR DELIVERING BONE CONDUCTION STIMULI TO AND FOR MEASURING GRAVITATION RECEPTOR FUNCTIONS OF THE INNER EAR

(71) Applicant: Ear and Skull Base Center, P.C., Portland, OR (US)

(72) Inventors: Phillip Ashley Wackym, Portland, OR (US); Ashton Rhys Wackym, Portland, OR (US)

(73) Assignee: Ear and Skull Base Center PC, Portland, OR (US)

( * ) Notice: Subject to any disclaimer, the term of this patent is extended or adjusted under 35 U.S.C. 154(b) by 0 days.

(21) Appl. No.: 14/276,939

(22) Filed: May 13, 2014

(65) Prior Publication Data

US 2014/0336449 A1    Nov. 13, 2014

Related U.S. Application Data

(60) Provisional application No. 61/822,694, filed on May 13, 2013.

(51) Int. Cl.
  *H04R 25/00* (2006.01)
  *A61B 5/00* (2006.01)
  *A61B 5/0484* (2006.01)

(52) U.S. Cl.
  CPC ........... *A61B 5/4023* (2013.01); *H04R 2460/13* (2013.01); *A61B 5/04845* (2013.01); *A61B 5/6814* (2013.01)

(58) Field of Classification Search
  USPC .......... 381/322, 326, 331; 600/25; 607/55–57
  See application file for complete search history.

(56) References Cited

U.S. PATENT DOCUMENTS

| 2004/0199214 A1 | 10/2004 | Merfeld et al. |
| 2008/0275513 A1 | 11/2008 | Lattner et al. |
| 2009/0292161 A1 | 11/2009 | Parker |

FOREIGN PATENT DOCUMENTS

| WO | 99-09881 | 3/1999 |
| WO | 2011-163115 | 12/2011 |

OTHER PUBLICATIONS

Bruel & Kjaer, "4810 Instruction Manual, Mini Shaker Type 4810", Printed in Denmark by Naerum Offset, English DK BE0515-12, Revision May 1987.
Nguyen et al., "Test-Retest Reliability and Age-related Characteristics of the Ocular and Cervical Vestibular Evoked Myogenic Potential Tests", NIH Public Access, Otol Neurotol, Author (unedited) Manuscript, 2010.

(Continued)

*Primary Examiner* — Suhan Ni
(74) *Attorney, Agent, or Firm* — Schwabe, Williamson & Wyatt, P.C.

(57) ABSTRACT

Disclosed herein are apparatus and methods for delivering bone conduction stimuli for measuring the gravitation receptor functions of the inner ear. In some embodiments, an apparatus may include (i) an impactor operatively linked to a guide disposed within a housing and (ii) an electrically driven actuator enclosed within the housing. The electrically driven actuator may be configured to cause the impactor to (i) travel to a striking point to deliver a mechanical bone conduction stimulus for transmission to a skull bone and (ii) controllably decelerate prior to the instance of stimuli delivery.

20 Claims, 21 Drawing Sheets

(56) References Cited

OTHER PUBLICATIONS

Wackym et al., "Rapid cVEMP and oVEMP Responses Elicited by a Novel Head Striker and Recording Device", Ear and Skull Base Center, and Legacy Research Institute, Portland, Oregon, USA, Otology & Neurotology, Inc., Otol Neurotol 2012;33:1392-400, 2012.

Knox, Glenn, "Response to Re: Rapid cVEMP and oVEMP Responses Elicited by a Novel Head Striker and Recording Device", Otology & Neurotology, vol. 34, No. 4, 2013.

SYSTEMS AND METHODS FOR DELIVERING BONE CONDUCTION STIMULI TO AND FOR MEASURING GRAVITATION RECEPTOR FUNCTIONS OF THE INNER EAR

CROSS-REFERENCE TO RELATED APPLICATION

The present application claims priority to U.S. Provisional Patent Application No. 61/822,694, filed May 13, 2013, and titled "APPARATUS AND METHOD FOR DELIVERING BONE-CONDUCTION STIMULI TO AND FOR MEASURING GRAVITATION RECEPTOR FUNCTIONS OF THE INNER EAR," the entirety of which is incorporated herein by reference.

TECHNICAL FIELD

The present disclosure relates to systems and methods for testing the inner ear, and more particularly, to systems and methods for delivering bone conduction stimuli to and for measuring gravitation receptor functions of the inner ear.

BACKGROUND

The inner ear is the innermost part of the ear. As shown in FIGS. 1A and 1B, sound is directed by the pinna 102 through the ear canal 104 to the eardrum 106. The eardrum 106 moves the bones of the middle ear 108 to vibrate the cochlea. The cochlea generates electric pulses that are correlated with the sound, and these electric pulses are sent to the brain. The inner ear further includes a balance sensing system 110, referred to as the vestibular system. The vestibular system 110 generally includes three semicircular canals 112 and two pairs of otolithic organs (each located on a different side of the head). Each pair of otolithic organs includes a utricle 116 and a saccule 118. Internal to the semicircular canals 112 and surrounding the otolithic organs are the endolymphatic ducts containing endolymph. Multiple ampullae 120 may also be disposed in the inner ear. The semicircular canals 112 may be characterized as providing three rotational receptors (the ampullae 120) and two gravitational receptors (the otolithic organs 116, 118). The semicircular canals 112 and the otolithic organs 116, 118 in the inner ear contain hair-cell transduction mechanisms that, for example, help (i) provide the brain with spatial orientation cues, (ii) keep the eyes focused on a target when the head is in motion, and (iii) maintain balance. Specifically, the ampullae 120 of the semicircular canal 112 respond to rotations, while the otolithic organs 116, 118 sense linear accelerations, decelerations, and tilting. As a result, stimulations of normal otolithic organs, specifically, the utricle 116 and saccule 118, will produce a response in (i) the eye muscles to allow the eyes to maintain gaze and (ii) the muscles that contribute to movement of the head.

Gravitational receptor asymmetry produces dizziness, a sense of motion, tilting, being pushed, pulled or falling; while rotational receptor asymmetry produces true rotational vertigo. Ninety million Americans go to health care providers because of vertigo, dizziness, or balance problems. It is the second most common complaint heard in doctor's offices, and will occur in 70% of the nation's population at some time in their lives. Falls account for 50% of accidental deaths in the elderly, and 10% of falls result in hospitalization. Every 15 seconds, an older adult is treated in the emergency room for a fall; every 29 minutes, an adult dies following a fall. Research has indicated that the annual direct and indirect costs of fall-related injuries are estimated to reach $54.9 billion by the year 2020, and that participants with vestibular dysfunction who were symptomatic, i.e., reported dizziness, independently increased the odds of falling more than 12-fold. Research has also indicated that increasing age is associated with an increased prevalence of vestibular dysfunction. There are also military considerations with post combat-induced injuries and loss of military aircraft and other assets that contribute to the scope of vestibular related problems.

It is known that bone-conducted stimulation to the head, as well as auditory stimulation, excites the otolithic organs 116, 118. As a result of the stimulation, a response (e.g., action potential) is produced at the sternocleidomastoid muscle (a neck muscle that contributes to the movement of the head) and the extraocular muscles (eye muscles that allow the eyes to move and focus). In addition, inhibitory or excitatory action potentials are produced at other muscles (e.g., triceps or splenius capitus muscles) in response to activation of the two otolithic organs. A muscle response may be characterized or measured as an electrical impulse from the brain to the muscles. Specifically, a cervical vestibular evoked myogenic potential (cVEMP) response has been observed to be an inhibitory response, measured at the sternocleidomastoid muscle, corresponding to an activation of the saccule 118. Also, an ocular vestibular evoked myogenic potential (oVEMP) response has been observed to be an excitatory response, measured at the inferior oblique muscle (an extraocular muscle that controls a specific movement of the eyes), corresponding to an activation of the utricle 116. The extraocular muscles include six muscles, including the inferior oblique, superior oblique, medial rectus, superior rectus, inferior rectus, and the lateral rectus muscles. By observing the cVEMP and oVEMP response, it is generally known that diseases, disorders, and conditions affecting the vestibular system and the balance sensing system of a person may be observed.

Besides producing auditory stimuli, some in the art have developed various types of apparatus to deliver bone conduction stimuli to certain parts of the skull bone (e.g., the frontal bone, the parietal bone, the occipital bone) to test the gravitational receptor functions of the inner ear. For example, some in the art have employed electromechanical devices and mini-shaker apparatus. Such apparatus have been observed to produce stimuli of insufficient magnitude to elicit a robust response. Some in the art have also employed solenoid actuators. Existing arrangements including solenoid actuators may produce stimuli of sufficient magnitude, but may also produce other stimulations of the otolithic organs for certain patients. Some have used reflex hammers. Of these conventional approaches, the reflex hammer tapping of the forehead may produce the most robust cVEMP and oVEMP responses, but there is no mechanism to standardize and calibrate the stimulus.

Bone conduction stimulus may be applied at various locations on the head, for example, at the front of the forehead along the mid line. FIGS. 1C and 1D illustrate example electrode placement diagrams for delivery of bone conduction stimuli. The bone conduction stimuli may be applied at the same location among different patients and among different tests in order to improve the repeatability of the testing, for example, at the "Fz" location 120.

BRIEF DESCRIPTION OF THE DRAWINGS

The foregoing features of embodiments will be more readily understood by reference to the following detailed description, taken with reference to the accompanying drawings, in which.

DETAILED DESCRIPTION

Figure 1A:
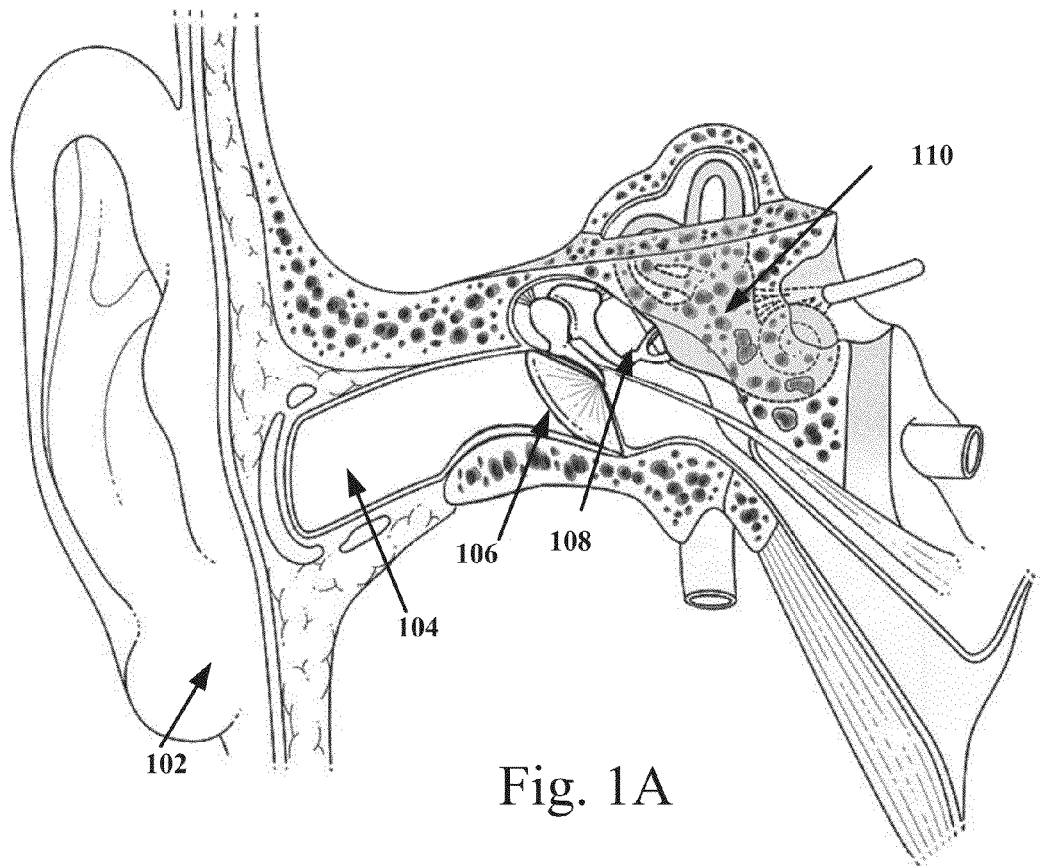
FIGS. 1A and 1B illustrate various anatomical structures associated with the human ear and inner ear.
Figure 1B:
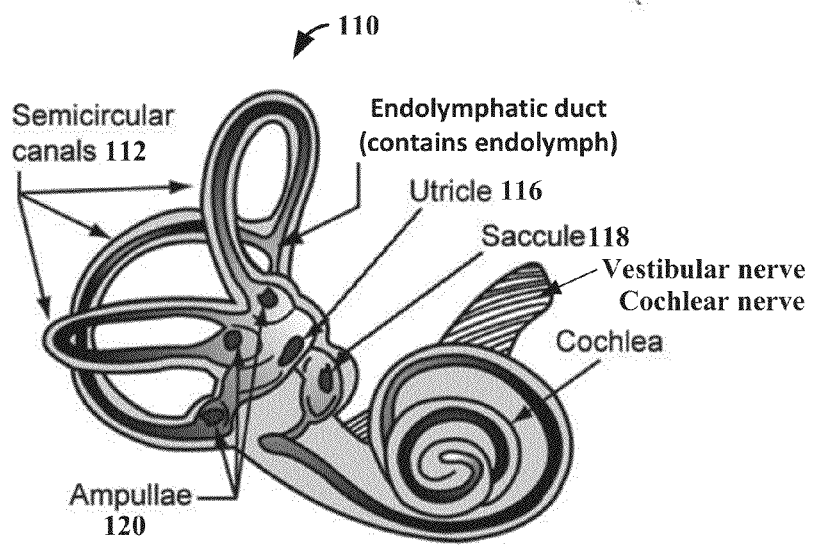
Figure 1C:
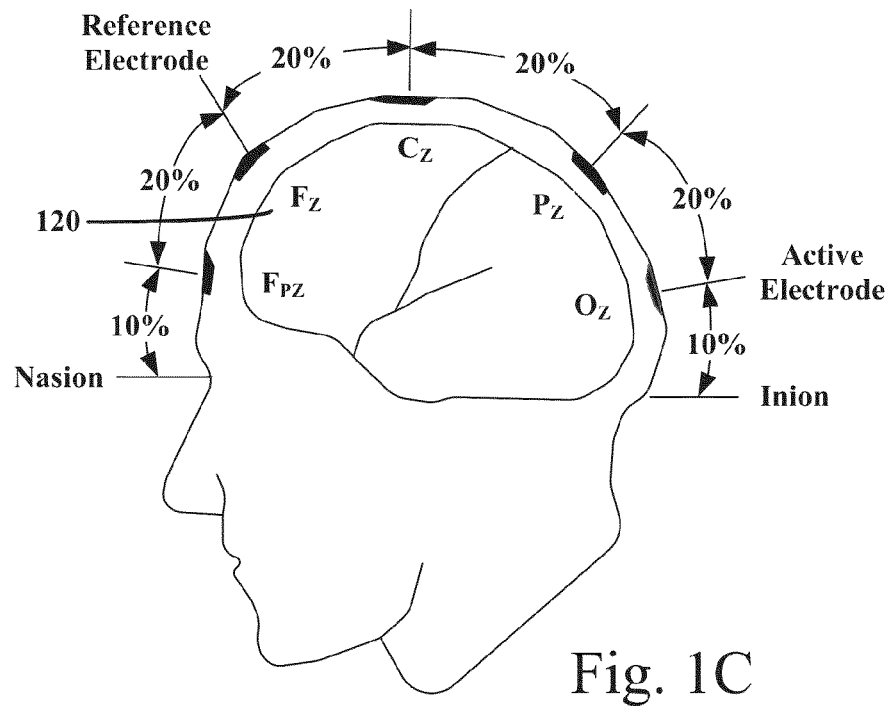
FIGS. 1C and 1D illustrate example electrode placement diagrams for delivery of bone conduction stimuli.
Figure 1D:
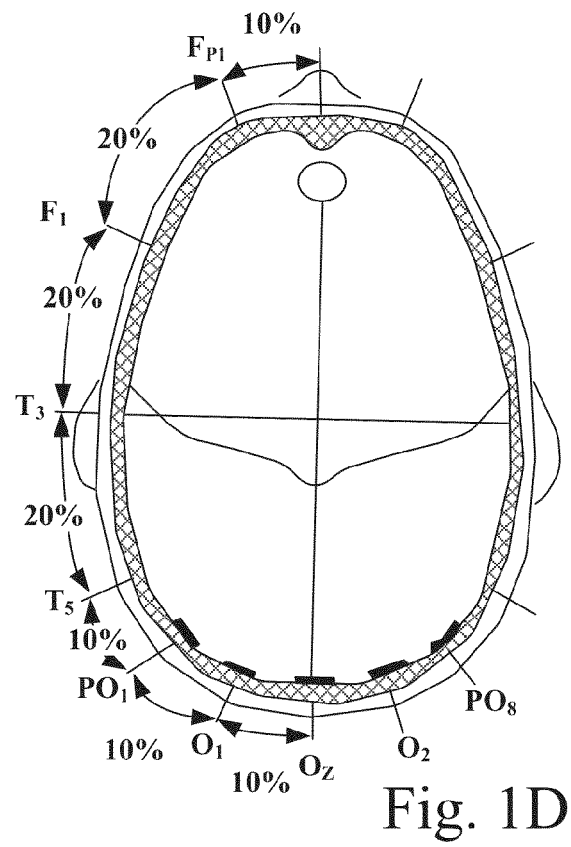

As used herein, the term "gravitation receptor functions" may refer to operations of the vestibular system, such as the provision of perception and monitoring of gravity, acceleration, deceleration, orientation, balance, and movement. The term may also refer to physiological response resulting from the stimulation of the vestibular system, such as the cervical vestibular evoked myogenic potential (cVEMP) or the ocular vestibular evoked myogenic potential (oVEMP).

As used herein, the term "stimuli" may refer to a series of distinct forces or impulses applied to a person to measure or test the gravitation receptor functions of the person's inner ear. Each force may be generated by a mechanical impact applied to the skull bone of a person (e.g., a patient) and may be conducted through the skull bone to the inner ear to elicit a physiological response of the person's vestibular system. A subset of a stimuli having only one force is a stimulus.

As used herein, the term "patient" may refer to any person who is receiving a bone conduction stimulus or is being measured for the gravitation receptor functions of his or her inner ear.

As used herein, the term "cervical vestibular evoked myogenic potential," abbreviated as "cVEMP," may refer to an inhibitory response measured at the sternocleidomastoid muscle, corresponding to activations of the saccule.

As used herein, the term "ocular vestibular evoked myogenic potential," abbreviated as "oVEMP," may refer to an excitatory response measured at the extraocular muscle (e.g., the inferior oblique muscle), corresponding to activation of the utricle.

As used herein, the term "skull bone" may refer to a subset of bones of the head including the frontal bone, the parietal bone, and the occipital bone.

In an exemplary embodiment, a method and apparatus may provide a stimulus to the skull bone in a manner that does not contaminate, or interfere with, a measurement of the resulting physiological response of the person's vestibular system (i.e., gravitational receptor functions). To provide such a measurement, the stimulus may be generated in a manner so as to not produce an auditory response of the ear. Herein, various embodiments of the present disclosure recognize that bone conduction stimulation (performed without auditory stimulation) may produce a more robust response of the gravitation receptor in the inner ear relative to the conventional noise-masking and noise-normalizing techniques known in the art. In particular, various embodiments of the present disclosure recognize that stimulation of the auditory system may produce a response of the gravitation receptor in the inner ear, which may interfere with and/or contaminate the response from bone conduction stimulation. This stimulation of the auditory system may be referred to as "air-conduction stimulation" and is the result of sound waves (i.e., an "air-conduction" stimulus) that stimulates the eardrum, rather than a force generated by a mechanical impact to the skull bone that is conducted through the skull bone to the inner ear. To avoid triggering an auditory response of the ear during bone conduction stimulation, embodiments of the apparatuses disclosed herein may operate in a generally silent manner. In addition to being substantially silent, various embodiments may be configured to deliver more impacts (up to 500% more relative to systems known in the art) at scalable impact intensity, enabling higher fidelity measurements than previously achievable. Thus embodiments disclosed herein may be advantageous for testing the human balance sensing receptors in the inner ear, and more particularly, to testing otolithic responses.

Various embodiments of the apparatuses disclosed herein may be portable and may be configured for fast deployment. In field testing, it has been observed that various embodiments of the apparatus may be administered faster than traditional acoustic cVEMP and oVEMP systems. In addition to providing substantially interference-free or contamination-free measurement, various embodiments may sufficiently saturate the gravitational receptor so that inter-aural differences are more accurate and consistent, thereby reducing variability among tests. Such saturation has been described in P. A. Wackym et al., *Rapid cVEMP and oVEMP Responses Elicited by a Novel Head Striker and Recording Device*, 33 OTOL. NEUROTOL. 1392-1400 (2012), which is incorporated by reference herein in its entirety.

In some embodiments, the methods and apparatuses disclosed herein may provide for consistent and quickly deployable measuring of the oVEMP and cVEMP responses. Specifically, various embodiments may be deployed for a measurement (or series thereof) in less time relative to conventional protocols.

In one aspect, a method and apparatus may provide for consistent and quickly deployable measuring of action potential of the extraocular muscles (e.g., oVEMP). To enable such a measurement, the apparatus may be adapted to be quickly and easily seated (like a mask) over at least a portion of a patient's face. An electrode (or plurality thereof) may extend from the apparatus and may be situated over at least a portion of the extraocular muscle of at least one eye. In some embodiments, other sensors (e.g., accelerometers) may be coupled to the apparatus and may provide data useful for normalization and/or feedback, as discussed below. The apparatus and electrode may not impinge on the globe of the eye or the extraocular muscle nor limit motions of the globe, and thus may provide for a clearer and more robust measurement of the oVEMP response than conventional approaches.

In another aspect, a method and apparatus may provide for consistent and quickly deployable measuring of action potentials of the sternocleidomastoid muscles (e.g., cVEMP). To enable such a measurement, the apparatus may provide a resting area for the patient's chin while causing the patient to lean (i.e., tilt or bend) forward. In doing so, the apparatus may cause the patient to flex his or her neck in a manner that causes a portion of the sternocleidomastoid muscles to contract. The cVEMP response is an inhibitory response, and thus the sternocleidomastoid muscles should be contracted during the measuring or testing to detect the inhibition. By providing assistance and/or support to reduce strain during the measurement, particularly for certain patients (i.e., impaired or injured), such embodiments may enable robust and consistent measurements.

Existing protocols typically require the patient to lie supine while flexing his or her neck and turning his or her head against resistance. For certain patients (e.g., elderly patients, or patients suffering from kyphosis), this protocol may be more than uncomfortable. Such patients may not have the physical stamina to maintain the suspension and flexion of their neck for the duration of the testing or measurement. Additionally, such protocols may aggravate ailments, such as temporomandibular joint dysfunction, due to the excessive force applied to the joint while the patient is turning his or her head against resistance. The present embodiment alleviates such strain and provides the patient with a more comfortable testing position by allowing contraction of the sternocleidomastoid muscles without straining the temporomandibular joint and/or neck and spine.

In another exemplary embodiment, a method and system may provide for novel measurement schemes, such as measurement of an input-output function of the gravitational receptor functions as well as measurements with normalized responses. A normalized-response measurement may be advantageously employed in a clinical or research protocol to determine subtle defects of the gravitational receptors and differences thereof. The input-output function of the gravitational receptors has not been previously studied. These apparatus may also provide capabilities for more frequent stimuli-delivery than achievable with conventional approaches.

Figure 2:
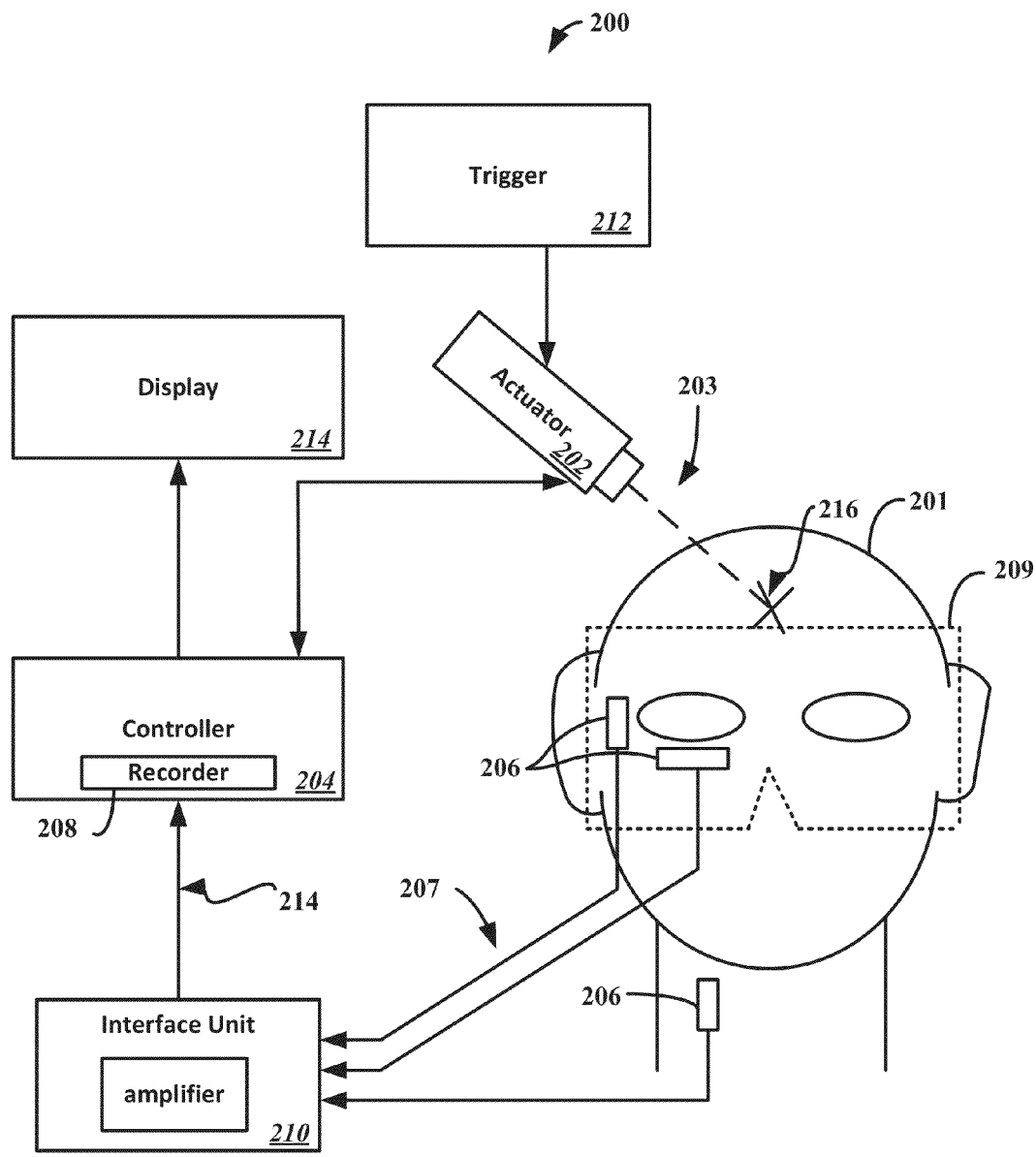
FIG. 2 illustrates a system for measuring gravitational receptor functions of the inner ear, according to various embodiments.

FIG. 2 illustrates a system 200 for measuring gravitational receptor functions of the inner ear, according to various embodiments. The system 200 may include an electrically driven actuator 202 (shown as "actuator 202") to deliver a bone conduction stimulus 203 (or a sequence thereof) to a location 216 of the head of the patient 201 and thus to the skull bone of a patient 201. The system 200 may include a controller 204 to actuate the electrically driven actuator 202. In some embodiments, the controller 204 and the electrically driven actuator 202 may form an electrically driven actuator system. In some embodiments, the electrically driven actuator system may further include the interface unit 210 (discussed below). The electrically driven actuator 202 may be adapted to deliver the bone conduction stimulus 203 in a manner that substantially only induces bone-conducted stimulation and does not induce a substantial auditory stimulation. The auditory stimulation may be of a negligible magnitude so as to not contaminate or interfere with the measured response resulting from the bone conduction stimulation. As such, the electrically driven actuator 202 may operate in a generally silent manner as compared to conventional actuator arrangements used in the art (e.g., conventional solenoid actuator arrangements) while sufficiently saturating the gravitational receptor for more consistent measurement between different impacts and/or tests. In particular, conventional solenoid actuator arrangements have been observed to produce sound in the range of 70-80 decibels Hearing Level (dB HL). The electrically driven actuator 202 may produce a sound level between 29.2 dB HL and 50 dB HL, a substantial reduction. Noise suppressing earplugs and/or ear covers may be additionally employed to further reduce interference and contamination from auditory stimulation. As discussed herein, the electrically driven actuator 202 may also deliver stimuli more frequently than conventional solenoids, strengthening the ability to average the responses and reduce the impact of noise, and may also be configured to deliver scalable stimuli so that input-output functions can be calculated or activation thresholds (e.g., evoked potential thresholds; the amount of force and acceleration needed to achieve the maximal response) determined.

The controller 204 may be a computer system that operates measurement software configured to control the operation of the electrically driven actuator 202. For example, the controller 204 may be part of an off-the-shelf data acquisition system, such as those manufactured by National Instruments, Inc. (Austin, Tex.).

The system 200 may include a plurality of sensors 206. In some embodiments, one or more of the sensors 206 may be configured to measure a signal 207 corresponding to a response of the patient 201 to the bone conduction stimulus 203. The measured signal 207 may be any representation of a signal corresponding to a physical phenomenon, including a pickup or sensed signal from an electrode, and/or including any conversion, digitization, transformation, and/or filtering performed by a signal processing circuitry and/or a data processor on a measured signal (e.g., as discussed below with reference to the interface unit 210). For example, in some embodiments, the interface unit 210 may include a linear current amplifier, which may reduce the output force variability by over 90% relative to standard switching amplifiers. Any of the signals transmitted between different components of the system 200 may be transmitted via a wired or wireless communication channel. In some embodiments, wireless communication may take place using a short-range wireless communication protocol, such as Bluetooth.

One or more of the plurality of sensors 206 may be configured to seat over a portion of the extraocular muscle of at least one eye and/or a portion of one of the sternocleidomastoid muscles. In some embodiments, the measured signal 207 may correspond to an action potential of at least one of the muscles when that at least one muscle responds to the bone-conducting stimulus and/or stimuli. In some embodiments, sensors 206 may be included in a mask 209 adapted to seat over at least a portion of the face of the patient 201. The sensors 206 may include one or more preamplified electrodes. An example of a surface preamplified electrode that may be included in the sensors 206 is the Z03 EMG preamplified electrode manufactured by Motion Lab Systems, Inc. (Baton Rouge, La.). In some applications, preamplified reusable electrodes may present challenges due to picking up additional electrical artifact. In such applications, the use of disposable electrodes and increased signal amplification before data is logged may remedy the issue.

An example of a mask 209 that may be adapted to include the sensors 206 is the Model No. 1720xxxx eye protector manufactured by BSN Sports (Dallas, Tex.). Another example of a mask 209 may be adapted from computer assisted designs and custom 3D printing. In some embodiments, the sensors 206 may be mounted on an articulating arm. An example of a suitable articulating arm may include positioners, such as the Part No. PPM100 articulating arm manufactured by Tektronix, Inc. (Beaverton, Oreg.). An articulating arm may be coupled to a base and provide at least three-axis freedom of movement. Various types of articulating arms may be employed, which may be manually operated or computer-operated. Another example of an articulating arm on which the sensors 206 may be mounted in some embodiments is the Model No. 96130 arm manufactured by Moffatt Products, Inc. (Watertown, S. Dak.).

In some embodiments, the sensors 206 may include one or more sensors configured to provide impact-related feedback to the interface unit 210 and the controller 204. For example, the sensors 206 may include one or more accelerometers positioned on the head of the patient 201. These accelerometers may be configured to detect the acceleration of the portions of the head proximate to the accelerometers, and transmit this acceleration data back to the controller 204 and/or the interface unit 210. The controller 204 or the interface unit 210 may use the acceleration data to determine the forces experienced by the patient 201 during impact, in accordance with known physical principles. In some embodiments, the controller 204 or the interface unit 210 may use the acceleration data to normalize the response signal 207 (e.g., so that responses to higher force impacts can be properly compared to responses to lower force impacts). In some embodiments, the controller 204 may use the acceleration data to adjust subsequent impacts to achieve a desired force (e.g., in a feedback loop, as understood in the art). In some embodiments, one or more accelerometers may be mounted on each of the mastoid bones to generate data indicative of the force delivered to the temporal bone.

The system 200 may include a recorder 208 (shown as part of the controller 204) to receive the signal 207 from the sensors 206. The sensors 206 may interface to the controller 204 via an interface unit 210, which may include amplifiers and/or signal processing circuitry configured to process and/or enhance the measured signal 207. The interface unit 210 may be a custom unit or a commercially available component. An example of the interface unit 210 that may be suitable for some embodiments is a multifunction data acquisition system (DAQ), such as the Model No. NI USB-6009 multifunction DAQ manufactured by National Instruments, Inc. (Austin, Tex.), which has, among other features, eight 14-bit analog-input channels that can each record 48,000 samples per second. The interface unit 210 may include buttons, knobs, displays, and other user interface elements that may be operated and/or viewed by an operator of the system 200 to observe measurements made or change the characteristics of the stimuli delivered by the system 200. For example, a knob or slider on the interface unit 210 may be coupled with the controller 204 so that rotations of the knob or translations of the slider may cause the force of the delivered stimuli to increase or decrease.

The system 200 may include a trigger 212 to initiate the electrically driven actuator 202 to deliver the bone conduction stimulus 203. In an embodiment, the trigger 212 may be an electrical switch operatively mounted on the actuator 202. The switch may be linked to the controller 204 to trigger a signal to the controller 204 when actuated. In addition to, or in lieu of, the trigger 212 operatively mounted on the actuator 202, the trigger 212 may be a part of the user interface of the controller 204. For example, the trigger 212 may include tangible buttons on a console or keypad or a graphically displayed button shown on a display 214. In another embodiment, the trigger 212 may be part of a remote switch adapted to be actuated by an operator's extremity. The remote switch may be situated on the floor as a foot pedal or a table top as part of a hand console. As such, the trigger 212 may be operated by the operator's hand or foot. An operator may be any person who is conducting or assisting in the measuring or testing of the gravitation receptor function using the system 200. In another embodiment, the trigger 212 may be part of a voice-recognition system having a microphone and voice-processing system to allow for voice-actuated triggering. Various voice-recognition system and voice-actuated triggering are generally known in the art and may be employed within various embodiments. The microphone may provide an audio signal to the voice-processing system. The voice-processing system may be part of the controller 204. The voice-processing system may include a processor configured to analyze the audio signal to determine presence of a command corresponding to actuation of the trigger 212. Upon determining that a voice command has been issued to trigger the actuation, the processor may cause a trigger signal to actuate the electrically driven actuator 202. The trigger signal may be provided to the controller 204.

In some embodiments, the system 200 may include a sensor disposed on or proximate to the electrically driven actuator 202 to output an electrical signal to the controller 204 when an impactor coupled to the electrically driven actuator 202 is proximal to the striking point. The electrical signal may be received by the controller 204 and may trigger a recording of an action potential at the patient 201, the action potential corresponding to the gravitation receptors of an inner ear of the patient 201.

The system 200 may include a display 214 to present the measured response. The display 214 may include capacitive or other tactile sensors, and thus may receive operator inputs (e.g., to select shapes and amplitudes of various waveforms, as discussed below). Examples of various displays are discussed below.

The system 200 may be configured to allow for rapid field testing of both gravitation receptors in each inner ear. Each of the two gravitational receptors (i.e., the saccule and utricle) may be tested individually or simultaneously on one side. Alternatively, all four receptors may be tested simultaneously and bilaterally. Simultaneous testing may be employed for quantitative assessment, and bilateral testing may be employed for rapid bedside screening of peripheral gravitational receptor functions. As such, a cVEMP response, an oVEMP response, or both, may be measured simultaneously, or in sequence, for one or both sides of the head.

In an illustrative embodiment, the actuator 202 may part of a handheld device, enclosed in a casing, to allow for easy manipulation and delivery of the bone conduction stimulus 203. The stimulus 203 may be a pre-determined force and/or momentum. In embodiments in which the actuator 202 has a longitudinal axis, the force of the stimulus 203 may be applied along an axis parallel or angled with reference to the longitudinal axis of the actuator 202, or along an arcuate path. In some embodiments, the actuator 202 may be coupled to a head-band configured to align or support the actuator 202 during the delivery of the bone conduction stimulus 203. In some embodiments, the actuator 202 may be housed within a mechanically linked gantry that is hinge-ably mounted to a structure, such as a chair, a table, or the floor so that the generated stimulus can be delivered without the use of a handheld actuator device.

Some embodiments of the system 200 may be characterized as a rapid, computer-controlled and calibrated handheld device that can deliver a plurality of bone conduction stimuli 203. Several applications of the system 200 have been contemplated. It is noted that the described applications are merely illustrative and other applications relating to clinical screening, testing, and diagnosis of the inner ear are applicable. Examples of applications for the systems disclosed herein include, but are not limited to, screening to monitor ototoxic drugs being administered in the hospital or in an ambulatory setting (e.g., a chemotherapy unit), screening for patients being admitted to the hospital to determine abnormalities of either gravitational receptor and also between inner ears (which may be useful as a predictor of hospital falls). A review of pathological conditions that have been studied using VEMPs, and to which the system 200 may be applied, is presented in K. D. Nguyen et al., *Test-retest Reliability and Age-related Characteristics of the Ocular and Cervical Vestibular Evoked Myogenic Potential Tests,* 31(5) OTOL NEUROTOL. 793-802 (2010); P. A. Wackym et al., *Rapid cVEMP and oVEMP Responses Elicited by a Novel Head Striker and Recording Device,* 33 OTOL NEUROTOL. 1392-1400 (2012); and P. A. Wackym, Response to: Rapid cVEMP and oVEMP Responses Elicited by a Novel Head Striker and Recording Device. 34(4) OTOL NEUROTOL. 779-780 (2013).

Furthermore, it is recognized that evaluations of the temporal aspects of gravitational receptor responses (e.g., the latency between the measured signal and the stimuli) may be used as a precursor to diagnose some types of inner ear vestibular disorders. For example, it is observed that with some patients with some types of inner ear vestibular disorders, the wave morphology, present when a disease is active, deteriorates and returns to normal after surgical intervention. Similar disruptions in wave morphology can be seen with auditory brainstem evoked responses with certain auditory disorders. However, conventional stimulus techniques have made such morphologies challenging to detect. Various embodiments of the systems disclosed herein may enable the detection of altered wave morphology for the bone conduction stimulus-based VEMP in a manner that is more detectable than achievable with acoustic stimuli. As noted above, the altered wave morphology may be a marker of an inner ear disease, and may be detected more readily with various embodiments of the systems disclosed herein than conventional technologies. Similarly, it is also observed that a shorter latency of the cVEMP response may be present in superior canal dehiscence patients pre-operation and that the latency may return to normal after a surgical correction. cVEMP and oVEMP responses have been reported to change when recorded pre- and post-operations. Consequently, various embodiments of the systems disclosed herein may enable the detection of the shorter latency of the cVEMP response, and thus detection of superior canal dehiscence. In addition, various embodiments of the systems disclosed herein may have application in any audiology, otology/neurotology, and neurology, or otolaryngology practice as a diagnostic tool.

Figure 3:
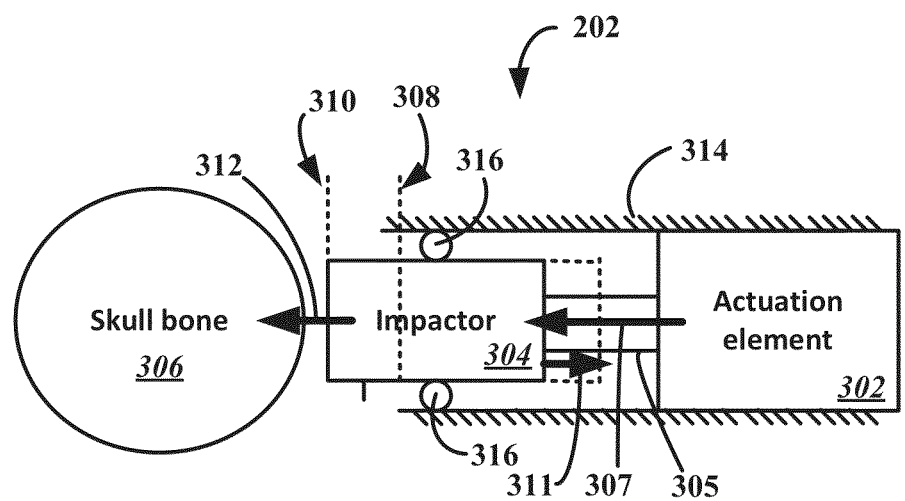
FIG. 3 illustrates an electrically driven actuator, according to various embodiments.

FIG. 3 illustrates an example of an electrically driven actuator 202, according to various embodiments. The electrically driven actuator 202 may include an actuation element 302 that is coupled to an impactor 304, for example, via a shaft 305. In some embodiments, the actuation element 302 may be rigidly coupled to the impactor 304. The actuation element 302 may be provided in a housing 314.

In use, the impactor 304 may transmit a force to a skull bone 306 of a patient 201 by impacting the skull of the patient 201. In some embodiments, the impactor 304 may be cushioned or malleable, and may act as a "hammer." An end of the impactor 304 that is closest to the skull during use may be formed as, for example, a pad. The impactor 304 may include a cushion material, such as a suitable polymer material or felt.

The actuation element 302 is configured to accelerate the impactor 304 in a direction 307 from a start location 308 to a striking location 310 so as to deliver a pre-defined force or momentum 312. The pre-defined force or momentum 312 may be of sufficient magnitude to saturate a gravitational receptor in the skull of the patient 201. For example, in some embodiments, a pre-defined force 312 may have a magnitude between 1 and 500 Newtons (N). The actuation element 302 may be adapted to operate in a near silent manner (e.g., less than 50 dB HL) when accelerating the impactor 304. In an embodiment, the actuation element 302 may be a voice-coil linear actuator. An example of a voice-coil linear actuator that may be included in the actuation element 302 in some embodiments is the Model No. NCC14-15-023-1PBS non-communication DC voice-coil linear actuator manufactured by H2W Technologies, Inc. (Santa Clara, Calif.). A voice-coil linear actuator may include a permanent magnet and a voice-coil that are adapted to move in relation to one another when the coil is powered. The magnet and voice-coil may be situated in a bearing system. In some embodiments, the actuation element 302 may include multiple voice-coil linear actuators operating as an array to increase the peak force that may be delivered. A voice-coil mechanism utilizes the relationship between electrical and magnetic fields to induce an axial force proportional to the driving current, and may have advantageously low friction force and high frequency loading that cannot be delivered by conventional pneumatic bone conduction systems. Minimizing bearing friction and maintaining a substantially linear voltage-to-force relationship during the entire stroke length may improve performance.

The striking location 310 (also referred to as a "striking point") refers to a position of the impactor 304 when the impactor 304 impacts the head. The start location 308 (also referred to as a "starting point") generally refers to a position of the impactor 304 prior to undergoing actuation by the actuation element 302. The striking location 310 may be located between the start location 308 and the location of maximum extension of the impactor 304 (i.e., the point along the path of travel of the impactor farthest away from the start location 308 in a direction toward the striking location 310). In some embodiments, the actuation element 302 may be adapted to decelerate 311 the impactor 304 as the impactor 304 approaches the striking location 310 to lessen the sound generated by the impact.

FIGS. 4A-4G illustrate various aspects of an example actuation element 302, according to various embodiments.

Figure 4A:
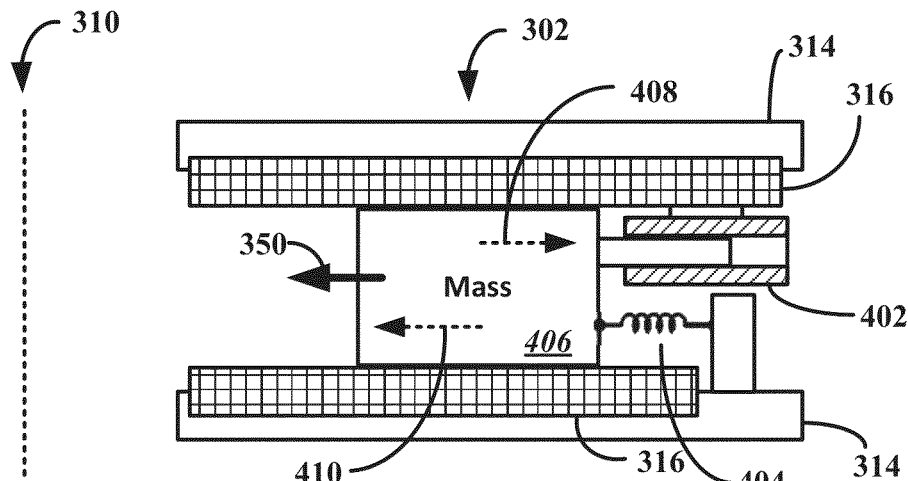
FIGS. 4A-4G illustrate various embodiments of the electrically driven actuator of FIG. 3.

The actuation element 302 may include an energy storage element to store potential energy to be release during the delivery of the stimulus. The energy storage element may be, for example, an electrical energy storage element (e.g., a capacitor) or a mechanical storage element (e.g., one or more springs). FIG. 4A illustrates an example actuation element 302 adapted to accelerate the impactor 304 (not shown) in a direction 350, according to various embodiments. The actuation element 302 of FIG. 4A includes an electrically-actuated assembly 402 (such as a solenoid or a voice-coil) and a spring assembly 404 arranged to accelerate a mass 406. The spring assembly 404 includes at least one spring (or a series thereof) that may be mounted to the housing 314. The mass 406 may be coupled to the impactor 304 such that an acceleration of the mass 406 results in an acceleration of the impactor 304. For example, the mass 406 may be rigidly coupled to the impactor 304 via the shaft 305. The actuation element 302 may have a travel length (measured between its point of travel farthest from the striking location 310 and its point of travel closest to the striking location 310) over which the actuation element 302 may travel so as to provide the mass 406 (and other bodies coupled thereto) with a pre-defined momentum (e.g., having a pre-defined velocity) at the time of stimulus delivery. To accelerate the mass 406, the electrically actuated assembly 402 may be energized with an electric potential having a first polarity to cause the mass 406 to move in a negative direction 408 (i.e., away from the striking location 310) to load the spring assembly 404 (e.g., put the one or more springs included in the spring assembly 404 into compression). Subsequently, the electrically actuated assembly 402 may be energized with an electric potential having a second polarity (opposite of the first polarity) to cause the mass 406 to move in a positive direction 410 (i.e., toward the striking location 310) to unload the spring assembly 404. In unloading, the spring assembly 404 augments the force in the direction 410 provided by the electrically actuated assembly 402 as a result of the application of the electric potential of the second polarity. The resulting force may be expressed as shown below in Equation 1, in which $F_{total}$ is the total force exerted on the mass 406, $F_{electrically-actuated\ assembly}$ is a force resulting from the electrical energy applied to the electrically-actuated assembly 402, and $F_{spring}$ is a force resulting from the unloading of the spring assembly 404.

$$F_{total} = F_{electrically-actuated\ assembly} + F_{spring} \quad (1)$$

$F_{spring}$ may be expressed as $\frac{1}{2}kx^2$ where k is a spring constant of the spring assembly 404, and x is a displacement in the negative direction 408, as understood in the art.

Figure 4B:
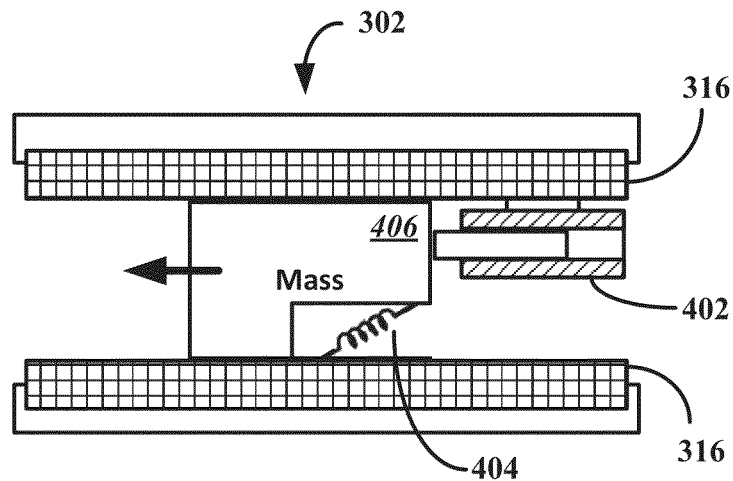

Alternatively, the actuation element 302 may be adapted with a spring assembly 404 that is loaded by being put in tension. An example of such an embodiment is illustrated in FIG. 4B.

Figure 4C:
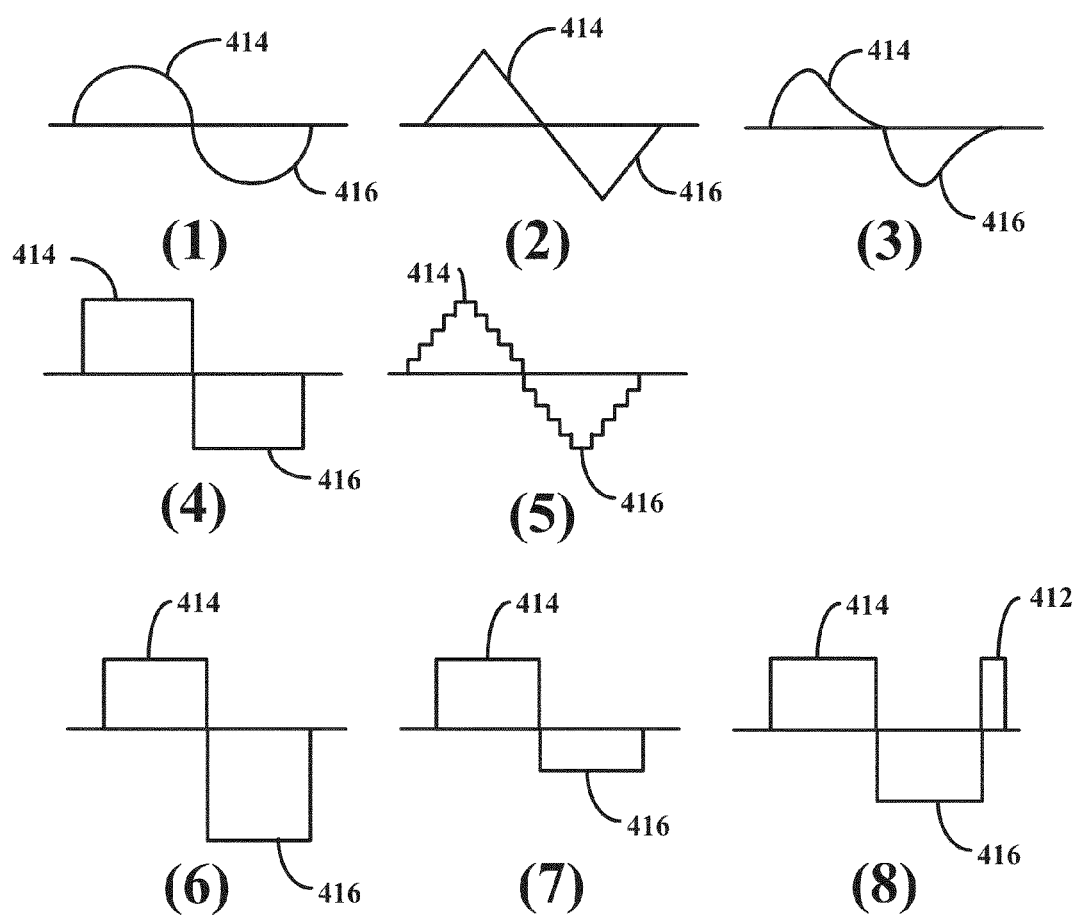

To provide the electric potential of the first or second polarity, the electrically actuated assembly 402 may receive a waveform of varying voltage and current from the controller 204 (not shown). For example, the waveform may be sinusoidal, triangular, stepped, skewed, or complex (e.g., a wavelet). FIG. 4C illustrates examples of various types of waveforms applied to the electrically-actuated assembly 402. Sub-figures (1) to (5) show various waveforms, including a sinusoidal, triangular, stepped, skewed, and square waveform. Portions of the waveforms on one side of the x-axis may have a first polarity and portions of the waveforms on the other side of the x-axis may have a second polarity. In particular, each waveform may include a first electric potential 414 having a first polarity and a second electric potential 416 having a second polarity, which is opposite of the first polarity. The peak voltage or current applied at the first and second polarity may also differ, examples of which are illustrated in sub-figures (6) and (7) of FIG. 4C. Differing peak voltages or currents may be employed to vary the magnitude of the bone conduction stimulus. The peak voltages or currents may be adjustable by an operator of the systems disclosed herein to adjust the magnitude (e.g., peak force or momentum) of the impact between the impactor 304 and the patient 201, thus providing a scalable impact. The differing peaks, shapes, averages, etc., may provide flexibility in the measurement or testing, and may allow practitioners to select the parameters of the measurement to perform different types of tests that may be suitable for different types of patients and/or conditions. For example, an operator may scale the impact in accordance with a patient's comfort level, or in accordance with other clinical guidelines. In some embodiments, the waveforms provided to the electrically actuated assembly 402 may be analog waveforms. In some embodiments, the waveforms generated by the controller 204 and provided to the electrically actuated assembly 402 may be generated by the controller 204 in a digital form, then converted to an analog form using a suitable analog to digital (A/D) converter.

In some embodiments, the electrically-actuated assembly 402 may receive a waveform of varying voltage and current from the controller 204 to assist both in positively accelerating the mass 406 toward the striking location 310 and in controllably decelerating the mass 406 prior to impact. For example, the waveform may include a portion having a third electric potential, subsequent to a portion having the second electric potential, having the first polarity. An example of this is illustrated in FIG. 4C subfigure (8), in which a first square wave portion (e.g., the first electric potential 414) having a first polarity is followed by a second square wave portion (e.g., the second electric potential 416) having a second polarity, and in which the second square wave portion 416 is followed by a third square wave portion 412 having the first polarity.

Referring back to FIG. 3, the electrically driven actuator 202 may include a housing 314 in which the actuation element 302 may be disposed. The impactor 304 may be disposed within or external to the housing 314.

Figure 4D:
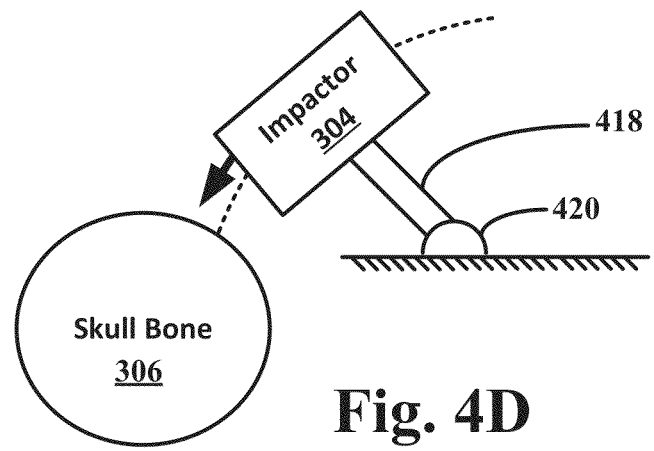
Figure 4E:
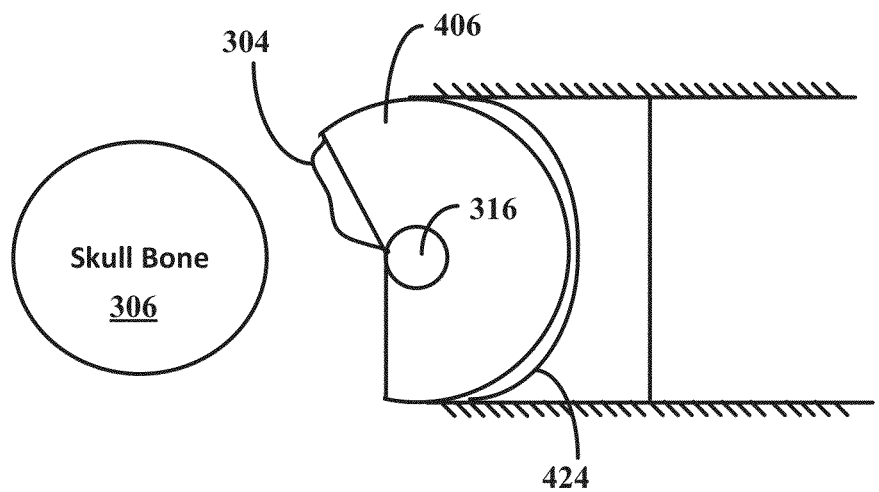

The housing 314 may include a guide 316 to maintain the orientation and alignment of the impactor 304 in relation to the actuation element 302. In some embodiments, the guide 316 may be a linear guide, which may be oriented parallel to or angled with reference to a longitudinal axis of the electrically driven actuator 202. FIGS. 4A and 4B, for example, show the guide 316, which may take the form of a bushing, sleeve bearing, journal bearing, or other suitable guide mechanism. In some embodiments, the guide 316 may take the form of a shaft that rotates around a hinge. For example, FIG. 4D depicts an embodiment in which the impactor 304 is coupled with a shaft 418 that rotates around a hinge 420 until the impactor 304 contacts the patient 201. In another embodiment, the guide 316 may allow for angular movements around a rotational axis. For example, FIG. 4E depicts an embodiment in which the guide 316 is as an axle holding a mass 406 in a socket 424. The impactor 304 may be coupled with a face of the mass 406 (e.g., as shown in FIG. 4E).

Figure 4F:
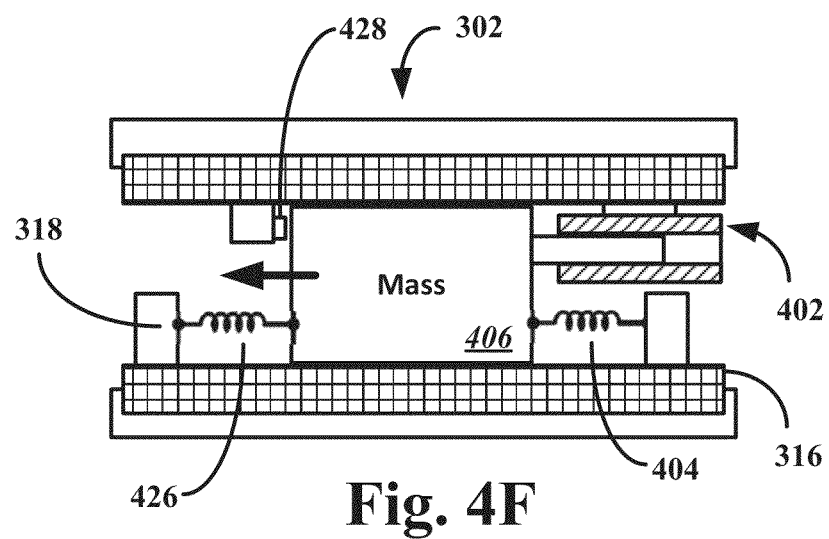
Figure 4G:
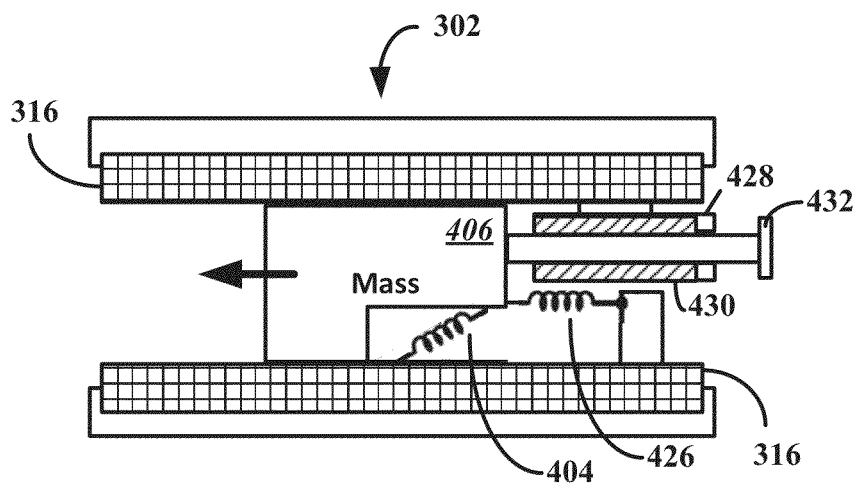

The electrically driven actuator 302 may include a deceleration element adapted to controllably decelerate the mass 406 prior to the impact of the impactor 304 and the patient 201, thereby allowing for near-silent operation. FIGS. 4F and 4G each illustrate a portion of embodiments of an electrically driven actuator 302 including one or more deceleration elements. The deceleration elements may operate in conjunction with the decelerating function of the electrically-actuated assembly 402, discussed above. As shown in FIGS. 4F and 4G, the deceleration element may include a spring 426 (or a series thereof) adapted to remove energy from the impactor 304 and store it (e.g., in compression or tension) as the impactor 304 approaches the striking location 310. As also illustrated in FIGS. 4F and 4G, the deceleration element may include cushioning elements 428, such as an elastic or deformable stopper, adapted to insulate any moving components from non-moving components. For example, as shown in the example of FIG. 4F, the cushioning elements 428 may be situated to insulate the mass 406 from directly contacting a portion of the housing 314 or static components affixed thereto. As another example, as shown in the example of FIG. 4G, the cushioning elements 428 may be situated to insulate moving components within the electrically actuated assembly 402. In the embodiment of FIG. 4G, a cushioning element 428 may take the form of a stopper situated between a stationary component 430 and a non-stationary component 432 of the electrically actuated assembly 402). The deceleration element 318 may take any of these forms, and may aid in the controllable deceleration of the mass 406.

Figure 5A:
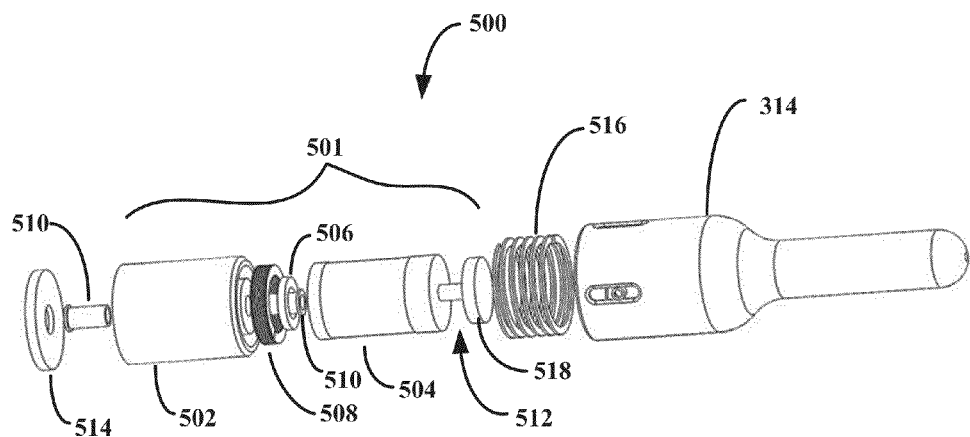
FIGS. 5A and 5B illustrate a handheld electrically driven actuator, according to various embodiments.
Figure 5B:
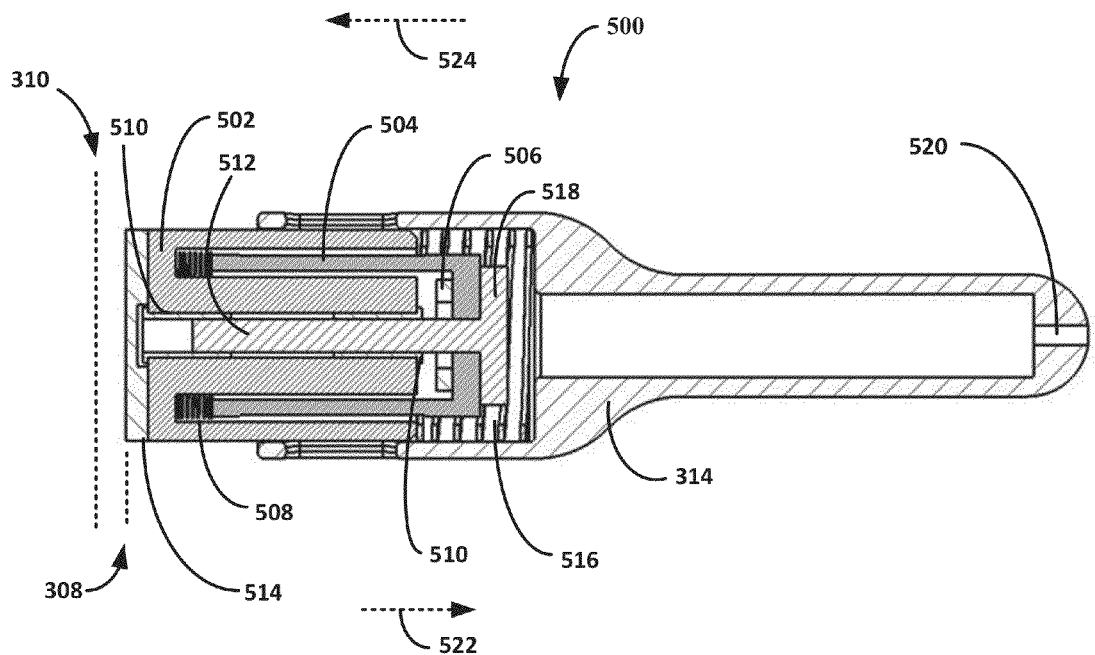

In some embodiments, the electrically driven actuators 202 disclosed herein may take the form of a handheld actuator. FIGS. 5A and 5B illustrate the electrically driven actuator 202 instantiated as a handheld actuator 500, according to various embodiments. FIG. 5A illustrates a disassembled view of the handheld actuator 500, and FIG. 5B illustrates a cut-out view of the handheld actuator 500 when assembled. As shown in the disassembled-view of FIG. 5A, the handheld actuator 500 includes a housing 314 that predominantly forms a body of the handheld actuator 500. A voice-coil linear actuator assembly 501 is provided as the actuation element 302. The voice-coil linear actuator assembly 501 may include a permanent magnet 502, a voice-coil 504, a polymer stopper 506, an impact spring 508, bushings 510, and a shaft 512. The handheld actuator 500 may also include an impact pad 514 (as the impactor 304) and contact force spring 516.

When assembled, and at rest (e.g., not energized), the voice-coil linear actuator assembly 501 may be secured substantially within to the housing 314. A locking screw (not shown) or other mechanism may be employed to retain the voice-coil linear actuator assembly 501 in relation to the housing 314. The voice-coil 504 and shaft 512 may be tapered against one another. The voice-coil 504 may be disposed in the permanent magnet 502 with the impact spring 508 and the polymer stopper 506 disposed therebetween. The voice-coil 504 may be arranged so as to be moveable relative to the permanent magnet 502. The permanent magnet 502 may have an inner bore that may be longitudinally aligned with the bushings 510. The shaft 512 may be disposed in the bushings 510 and may extend beyond the permanent magnet 502 to substantially permanently connect to the impact pad 514. The shaft 512 may have an elongated region and an end region 518. The end region 518 may be disposed against the contact force spring 516 that is situated between the voice-coil linear actuator assembly 501 and the housing 314. The housing 314 may include a cabling assembly 520 that allows for cabling (not shown) to connect the voice-coil 504 and the controller 204 (not shown). The cabling may include power and ground signal pathways. Other signal pathways may be included in the cabling to allow for communication of sensors and data signals from sensors (not shown) and on-board electronics (such as a trigger switch, not shown) situated in the handheld actuator 500. In some embodiments, some of the data transmitted between the handheld actuator 500 and the controller 204 or other components may be transmitted wirelessly using appropriate hardware included in the transmitting and receiving devices (e.g., Bluetooth hardware). In some embodiments, the handheld actuator 500 (or any of the actuators disclosed herein) may be battery powered.

During operation (e.g., the delivery of a bone conduction stimulus), the handheld actuator 500 may be positioned so that the impact pad 514 is proximate to the skull of the patient 201. In particular, the handheld actuator 500 may be positioned so that the striking location 310 is proximate to the desired impact point on the skull of the patient 201 (i.e., start location 308). The impact pad 514 may be positioned against the scalp of the patient 201 with a predetermined loading force, prior to application of an impact. In some embodiments, the predetermined loading force may be approximately 1.5 kilograms.

Power may be applied (for example, from the controller 204) at a first voltage polarity (e.g., positive) through the cabling to the voice-coil 504. The voice-coil 504 may generate a repulsive force with the permanent magnet 502 due to the power applied at the first voltage polarity, causing the voice-coil 504 to move in the loading direction 522, away from the striking location 310. In doing so, the voice-coil 504 may push the end region 518 of the shaft 512 (disposed against the voice-coil 504) to also move in the loading direction 522, thereby causing the contact force spring 516 to compress. The voice-coil 504 and permanent magnet 502 may be considered as the electrically actuated assembly 402 (as shown in FIGS. 4A and 4B) configured to accelerate the mass 406 (e.g., the voice-coil 504 and the shaft 512) while loading the spring assembly 404 (e.g., the contact force spring 516). The power applied at the first voltage polarity may be considered the first electric potential 414 (e.g., as shown in FIG. 4C). Actuator power may be limited to a safe and effective level by a hardware-coded limit setting on an amplifier, for example. In some embodiments, a software-coded power limit may also be included for redundancy.

After applying power at the first voltage polarity, a voltage of opposite polarity may be applied to the voice-coil 504. The power applied at the second voltage polarity may be considered the second electric potential 416 (e.g., as shown in FIG. 4C). In response, the voice-coil 504 may generate an attractive force with the permanent magnet 502, causing the voice-coil 504 to move in the impact direction 524 toward the striking location 310. With the repulsive force removed, the contact force spring 516 may stretch from its compressed state, thereby assisting or augmenting the force provided by the attractive force generated by the permanent magnet 502 and the voice-coil 504 in response to the power applied at the second voltage polarity. The resulting force may be characterized as discussed above with reference to Equation 1.

As the shaft 512 moves in the impact direction 524, the impact pad 514 may move toward the striking location 310. As the impact pad 514 approaches the striking location 310, the voice-coil 504 may begin to compresses the impact spring 508. The impact spring 508 may thus act as the deceleration spring 426 as shown in FIGS. 4F and 4G, and may controllably decelerate the mass 406 (e.g., the voice-coil 504 and the shaft 512). This controlled deceleration may prevent acoustic noise generated by a high-speed collision of two components of the handheld actuator 500, thereby allowing for near-silent operation of the handheld actuator 500 relative to conventional actuators. The polymer stopper 506 may be situated between the voice-coil 504 and the permanent magnet 502 and may act as a cushioning element 428 (e.g., as shown in FIGS. 4F and 4G), assisting in the controlled deceleration of the mass 406 (e.g., the voice-coil 504 and the shaft 512). The deceleration time may be short in comparison to the acceleration time, thereby having minimal effects on the impact energy. Audible impact noise may also occur during rebound. The mass 406 (e.g., the voice-coil 504 and the shaft 512) may be arranged to push against the contact force spring 516, which may act to prevent a rebound impact.

It should be appreciated by those skilled in the art that, in some embodiments, the voice-coil 504 and the permanent magnet 502 may operate to produce an attractive force therebetween to load the contact force spring 516 and then to produce a repulsive force therebetween to accelerate the impact pad 514 toward the striking point 310. It should also be appreciated by those skilled in the art that a voice-coil actuator having a static voice-coil and a moving permanent magnet may be employed rather than a static permanent magnet and moving voice-coil (as illustratively shown in FIGS. 5A and 5B).

The voice-coil 504 and shaft 512 may be considered to be suspended between two opposing springs (i.e., the contact force spring 516 and the impact spring 508). This suspension contributes to the silent or near-silent operation of the handheld actuator 500 by allowing for smooth and rapid transitions between each of the bone conduction stimuli. The polymer stopper 506 may provide further cushioning between moving components, though the components may be situated apart such that they do not contact each other between each delivery of a bone conduction stimulus. The impact pad 514 may be configured to contribute to the silent or near-silent operation of the handheld actuator 500. For example, in some embodiments, the impact pad 514 may include a wide surface area for impact (up to or greater than the cross-sectional area of the housing 314 of the handheld actuator 500). As such, energy from the handheld actuator 500 may be evenly distributed to the skull bone. Cushioning included on the impact pad 514 may also reduce acoustic noise.

As discussed herein, some embodiments of the handheld actuator 500 may enable delivery of bone conduction stimuli that are functionally silent, variable in force and impact, and purposely formed as modulated pulses. As such, the bone conduction stimuli may be synchronized with action potential recordings allowing for integrated data analysis, such as analysis to extract latency information between responses and other features of the measured response. It is observed that some embodiments of the handheld actuator 500 may operate at 4-10 hertz (Hz), which may be significantly faster than conventional solenoid-based cone conductions systems. As such, the handheld actuator 500 may enable more deliveries of the bone conduction stimuli in a given time period, allowing for a shorter testing protocol as well as opportunities for processing of the measured signal (e.g., averaging) to improve the signal-to-noise ratio of the measurement. For example, in some embodiments, testing using the handheld actuator 500 may be completed in ten minutes or less, a significant reduction relative to conventional approaches which may take thirty minutes or more. The shorter testing protocol may also make it easier for an operator holding the handheld actuator 500 to maintain the position of the handheld actuator 500 over the striking position on the patient's skull without drifting.

In alternate embodiments, either one of the two opposing springs (the contact force spring 516 and the impact spring 508) may be "pre-loaded" (i.e., under compressive or repulsive load when the handheld actuator 500 is de-energized). The pre-loading may be employed to bias the spring to increase or decrease the peak impact force that may be delivered by the handheld actuator 500. For example, the voice-coil linear actuator assembly 501 may be adapted to move in relation to the housing 314 to pre-load the contact force spring 516 at pre-defined increments along the housing 314. In some embodiments, the pre-load may also retain the mass 406 at the pre-defined start location 308 during rest. As such, when the voice-coil linear actuator assembly 501 is energized to load the contact force spring 516, a greater force may be released when the contact force spring 516 is unloaded.

Figure 6A:
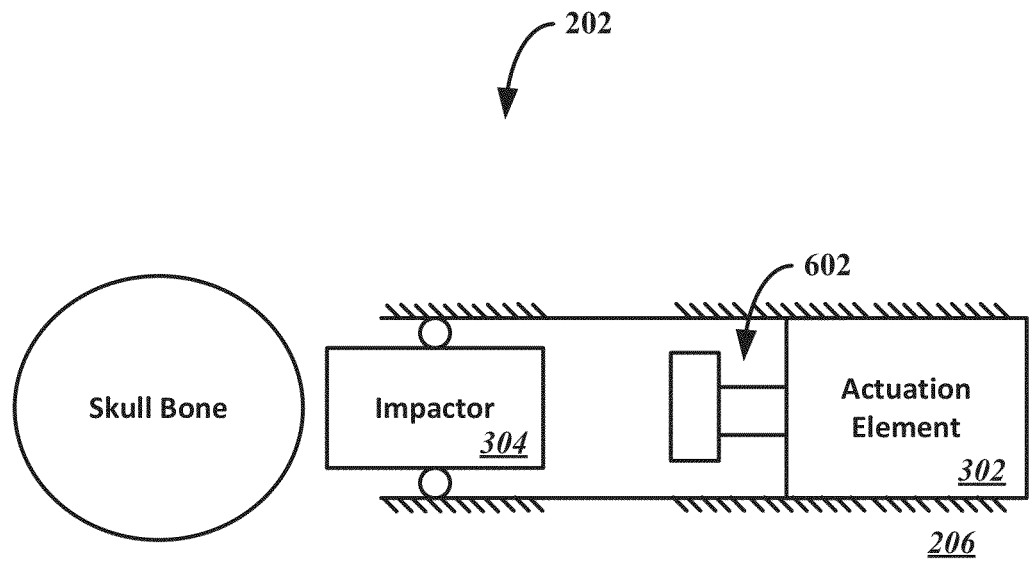
FIGS. 6A-6B illustrate electrically driven actuators, according to various embodiments.
Figure 6B:
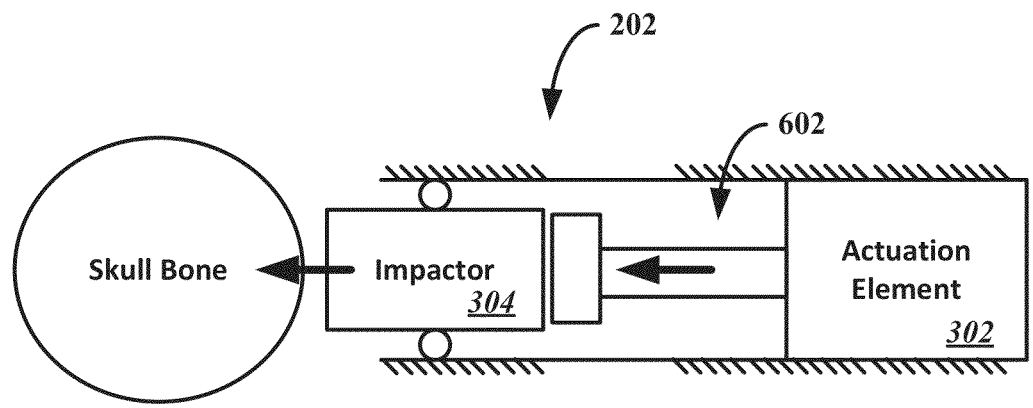

Other embodiments may deliver a bone conduction stimulus in a silent or near-silent manner. FIGS. 6A and 6B illustrate an electrically driven actuator 202 in two different positions, according to various embodiments. Rather than being rigidly coupled together (e.g., as discussed above with reference to the embodiments of FIGS. 5A and 5B), the impactor 304 may be movably coupled to the actuation element 302. The actuation element 302 may still be adapted to accelerate the impactor 304 from the start location 308 to the striking location 310 to deliver a pre-defined force or momentum. However, the actuation element 302 may accelerate an intermediate component 602 (e.g., a ram) that may transfer the kinetic energy of the actuation element 302 to the impactor 304. For example, FIG. 6A depicts the intermediate component 602 in a "retracted" position, and FIG. 6B depicts the intermediate component 602 in an "extended" position by which the intermediate component 602 may contact the impactor 304 and transfer the kinetic energy of the actuation component 302 to the impactor 304. As such, the impactor 304 may be modeled as an independent moving system relative to the actuation element 302.

As a result of the controllability of the handheld actuator 500 to deliver bone conduction stimuli that are variable in force and purposely formed as modulated pulses (e.g., by allowing the operator to select waveforms and amplitudes via the interface unit 210), the handheld actuator 500 may enable automated sequences of stimuli having varying waveform shapes, timing, and/or magnitudes for use in measurement and testing. FIGS. 7A-7D illustrate example testing sequences that may be used for measuring gravitation receptor functions, according to various embodiments.

Figure 7A:
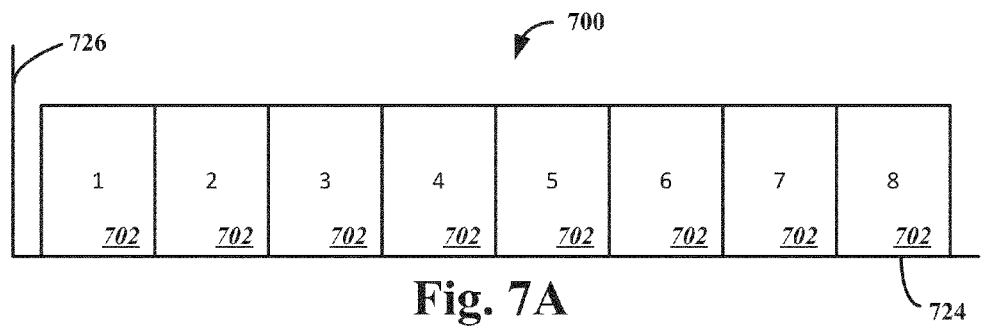
FIGS. 7A-7D illustrate example testing sequences for measuring gravitation receptor functions, according to various embodiments.

In some embodiments, a testing sequence may include stimuli of uniform peak magnitude, shape and duration. For example, FIG. 7A illustrates a plot (having an x-axis 724 representing time and a y-axis 726 representing delivered force) of a testing sequence 700 of different stimuli (referred to as "test signals") 702 with uniform peaks, shape, and duration. Each test signal 702 may be the product of a power waveform (e.g., the waveforms depicted in FIG. 3C).

Figure 7B:
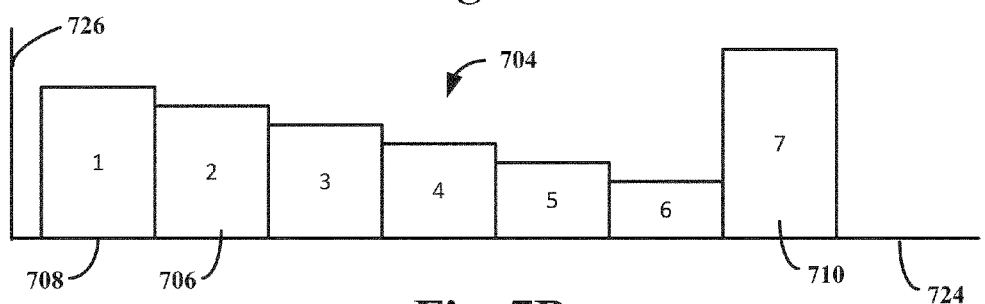

In some embodiments, the testing sequence may be a sequence of gradually varying stimuli (e.g., stimuli of increasing or decreasing amplitude and duration), such as a ramp. For example, FIG. 7B illustrates a plot (having an x-axis 724 representing time and a y-axis 726 representing delivered force) of a testing sequence 704 of test signals having gradually decreasing amplitude. For example, a second test signal 706 follows a first test signal 708 and has a lower peak or average amplitude. Similarly, subsequent test signals may have gradually increasing or decreasing amplitudes. For example, the peak, average, or other representative statistic of each test signal may differ by at least 20% between each consecutive test signal. Of course, other variations may be used. In one embodiment, the sequence 700 may include a fixed number n of test signals. In another embodiment, the test sequence 700 may be adaptive, in which test signals of decreasing amplitude are applied until no measured response (e.g., cVEMP and/or oVEMP) is observed. The test sequence 700 may include a last test signal 710, which may be a supramaximal stimulus (i.e., being of strength significantly above that required to activate all the nerve or muscle fibers in contact with one or more of the electrodes (e.g., included in the plurality of sensors 206). In some embodiments, a testing sequence may include a sequence of test signals of gradually increasing intensity (e.g., as quantified by the test signals' peak, or average) to determine the strength of the supramaximal stimulus.

Figure 7C:
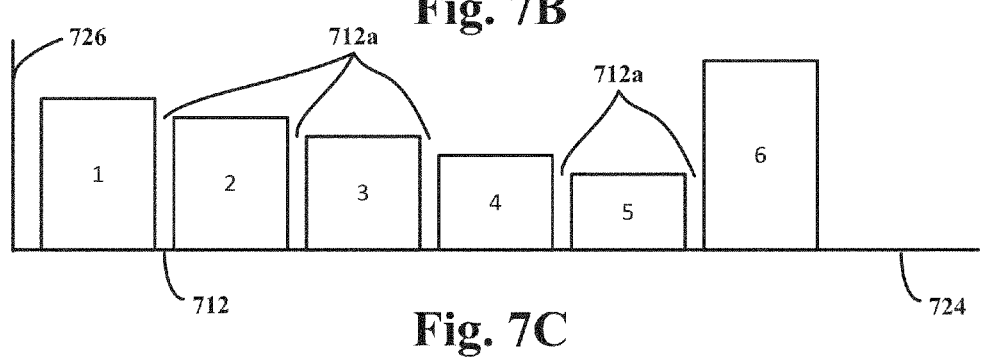
Figure 7D:
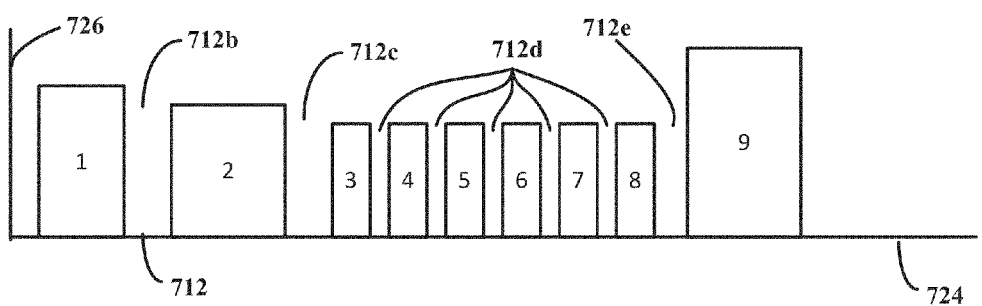

As shown in FIGS. 7A and 7B, the test sequence may form a continuous waveform. Alternatively, the test sequence may include pre-defined durations 712 between each of the test signals, as shown in FIGS. 7C and 7D. The pre-defined durations 712 may be consistent between the test signals in a test sequence, as shown for the durations 712a in FIG. 7C. The pre-defined durations 712 may vary between each test signal, as shown in FIG. 7D (as durations 712b, 712c, 712d, and 712e).

Figure 7E:
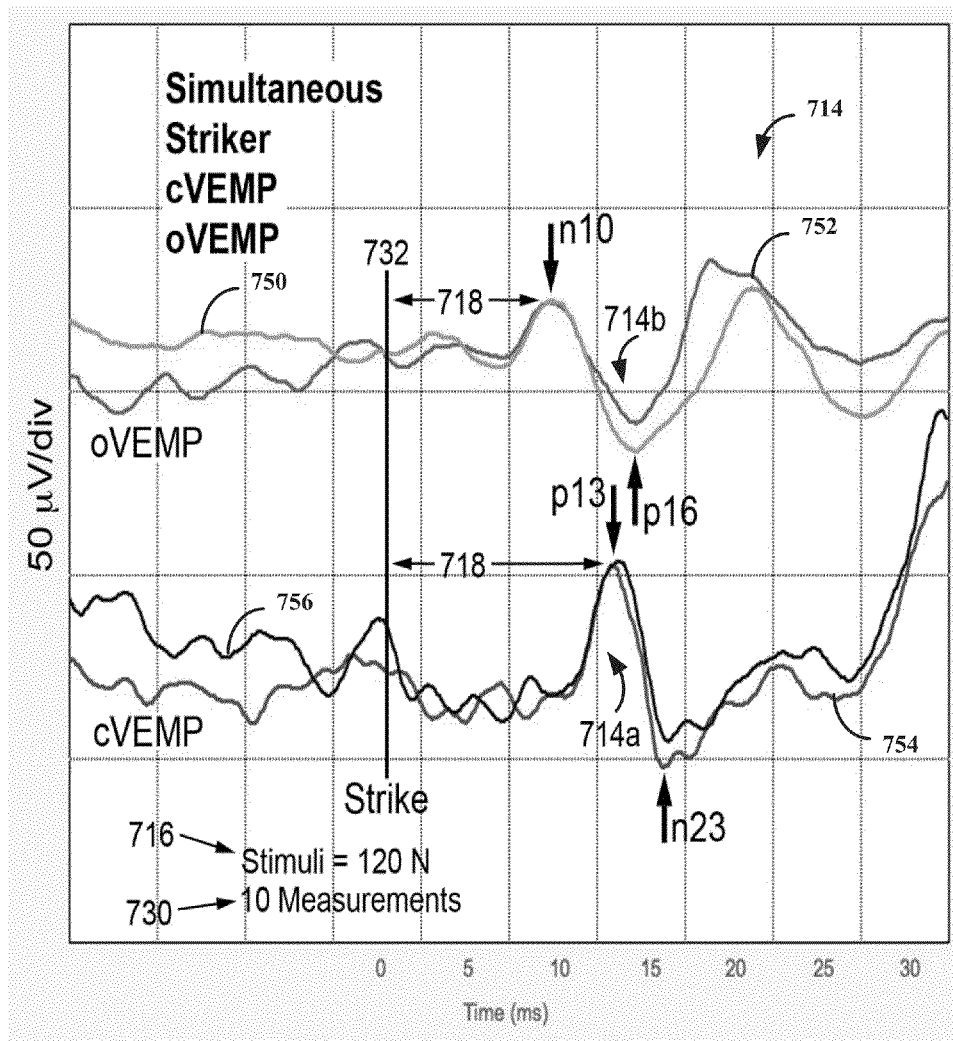
FIGS. 7E-7G show example outputs of a test employing one of the testing sequences illustrated in FIGS. 7A-7D, according to various embodiments.
Figure 7F:
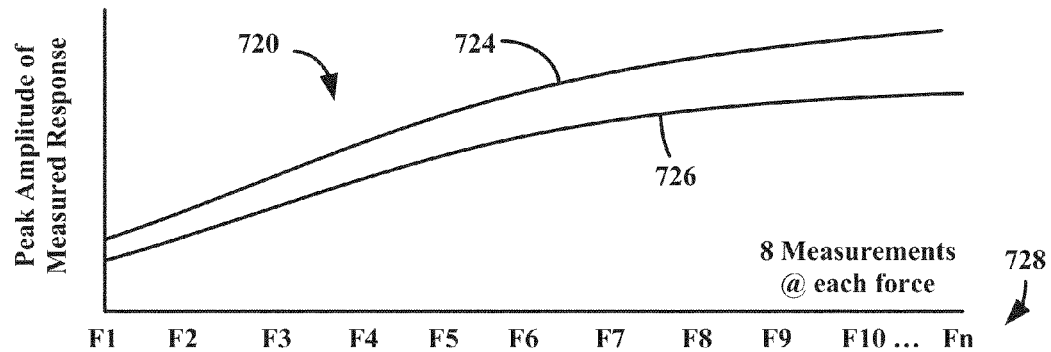
Figure 7G:
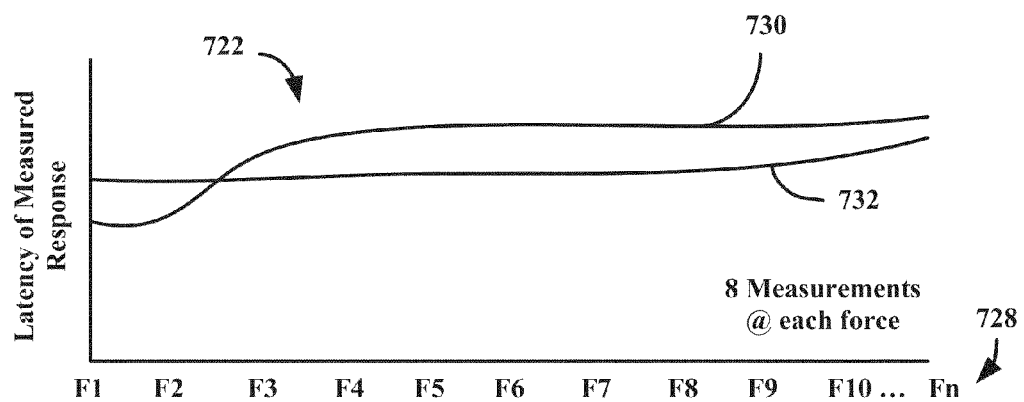

FIGS. 7E-7G illustratively show hypothetical outputs of a test of a patient's gravitational receptors in response to applying the testing sequence of FIGS. 7A-7D. Specifically, FIG. 7E illustrates a display 714 of one or more signals measured from the electrodes 206 (e.g., in response to the pattern of FIG. 7A). In some embodiments, the display 714 may include a representation of cVEMP 714a, oVEMP 714b, or both. The display 714 may indicate various characteristics of the test stimuli applied, such as (a) the peak force and/or momentum applied 716, (b) the number of stimuli applied 730, (c) the type of test sequence (e.g., ramp, adaptive, etc., not shown). The display 714 may indicate a time of initiation of delivery 732 and a time 718 (referred to as a latency time) between the initiation time 732 and an observed peaked measured response. For example, the oVEMP n10 potential may be identified as the first distinctive and replicated peak in the oVEMP waveform 714b, post-stimulus, and may typically occur around 8-12 milliseconds post-stimulus. The oVEMP p16 potential may be identified as the first distinctive and replicated trough in the oVEMP waveform 714b following the peak n10, and may typically occur around 16 milliseconds post-stimulus. The cVEMP p13 potential may be identified as the first distinctive and replicated trough in the cVEMP waveform 714a, post-stimulus, and may typically occur around 10-14 milliseconds post-stimulus. The cVEMP n23 potential may be identified as the first distinctive and replicated peak in the cVEMP waveform 714a, post-stimulus, and may typically occur around 19-23 milliseconds post-stimulus. The displayed signals may be an average of the signals (e.g., a windowed average). The display 714 may include statistical information, such as distribution, maximum range of amplitude and/or latency (e.g., normalized to stimulus intensity), minimum range of amplitude and/or latency (e.g., normalized to stimulus intensity), etc.

The oVEMP waveform 714b may include a left side oVEMP waveform 750 and a right side oVEMP waveform 75. The cVEMP waveform 714a may include a left side cVEMP waveform 754 and a right side cVEMP waveform 756. As shown, the system 200 may record the time of the initial strike and the time to the initial peak and then calculates the time difference; in the example of FIG. 7E, these time differences are 9.5 milliseconds (right side oVEMP waveform 752), 9.9 milliseconds (left side oVEMP waveform 750), 13.2 milliseconds (left side cVEMP waveform 754) and 13.7 milliseconds (right side cVEMP waveform 756).

FIGS. 7F and 7G illustrate hypothetical displays 720 and 722, respectively, of an input-output test, according to various embodiments. Impact patterns in which the stimuli varies (e.g., the patterns illustrated in FIGS. 7B-7D) may be used to perform an input-output test. FIG. 7F shows the amplitude (e.g., characterized by peaked magnitude, averaged magnitude, etc.) of a cVEMP measured signal 724 and oVEMP measured signal 726 on the y-axis, plotted against the stimuli (e.g., characterized by peak force, average force, peak momentum, average momentum, etc.) on the x-axis 728 (shown as "F1" to "Fn"). For example, the system 200 may acquire eight measured signals in response to 1 second of impacts delivered at 8 Hz at a given force, and may perform a set of such measurements at each of ten different forces for a total of ten seconds of testing and/or measurement. Each measurement for each given force may be averaged with the peak or average information being displayed. FIG. 7G shows the latency (e.g., the time 718 illustrated in FIG. 7E) of a cVEMP measured signal 730 and an oVEMP measured signal 732 on the y-axis, plotted against the stimuli (e.g., characterized by peak force, average force, peak momentum, average momentum, etc.) on the x-axis 728. Of course, various numbers of sets and numbers of measured signal per set may be employed. Clinicians may review these plots to identify unique patterns associated with Meniere's disease, the genetic loss of gravity receptor function, the development of ototoxicity during antibiotic or chemotherapy administration, superior canal dehiscence, or other conditions.

In some embodiments, the system 200 may be configured for novel measurement schemes and data analysis. For example, in some embodiments, the system 200 may compute and display an input-output comparison of the the gravitational receptor functions. An input-output comparison may be based on two or more impact patterns, each having different amplitude and/or frequency. The input-output comparison may analyze the difference between the patient responses to the two impact patterns, and present the difference in response as a function of the difference in impact pattern. The focus in some such comparisons may be on the relative differences in the amplitude or other characteristics of the two responses, rather than the absolute amplitudes or other characteristics of the responses. Such comparisons have not been previously studied, and may yield valuable clinical data.

In another example, the system 200 may compute and display normalized patient responses to various impact patterns (e.g., normalized to the average or maximum magnitude of the forces of the impacts in the impact pattern). The normalized response may be employed in a clinical or research protocol to determine subtle defects of the gravitational receptors and differences thereof.

In another aspect of some of the embodiments disclosed herein, various methods and apparatus may provide for consistent and quickly deployable measuring of the oVEMP. An apparatus may be adapted to be quickly and easily seated (like a mask) over at least a portion of a patient's face. One or more electrodes may extend from the apparatus and may be situated over at least a portion of the extraocular muscle of at least one eye, including the inferior oblique muscle. The apparatus and electrode may not impinge on the globe of the eye or the extraocular muscle, nor limit motions of the globe, thus providing for a clearer and more robust measurement of the oVEMP response. Commercial swim goggles may result in globe entrapment, and thus may be functionally useless for measurement purposes.

Figure 8:
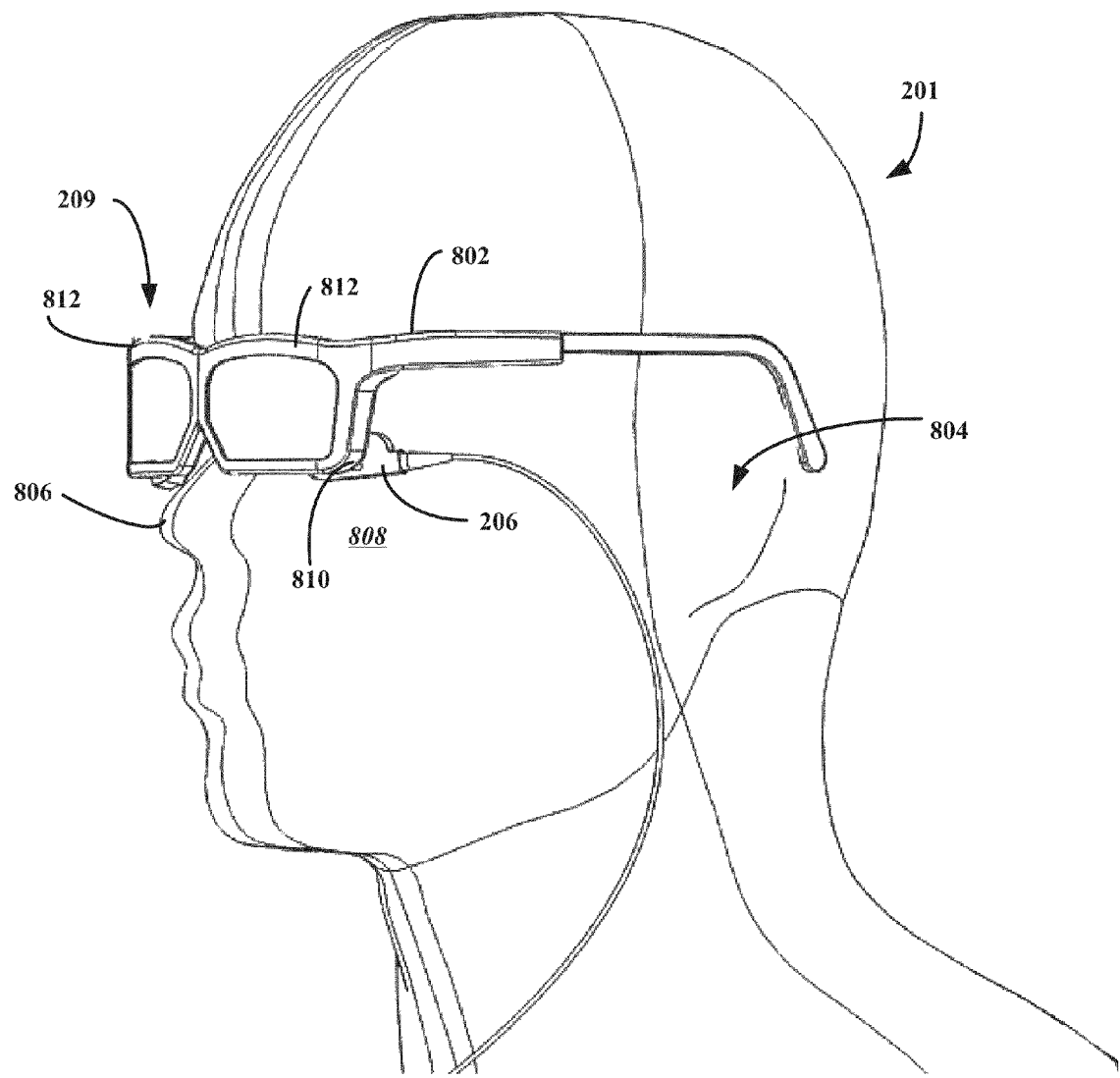
FIG. 8 illustrates an apparatus for measuring ocular vestibular evoked myogenic potential (oVEMP) response, according to various embodiments.

FIG. 8 illustrates a mask 209 for measuring oVEMP response, according to various embodiments. As used herein, a "mask" refers to any eyewear that, in use, seats over a portion of a face of a person without applying substantial pressure to the globes of the eyes and the extraocular muscles. A mask may be a cover, a protecting goggle, glasses, etc. Various ones of the mask embodiments disclosed herein may enable testing to be performed at a patient's bedside, rather than requiring the patient to travel to a designated testing location.

The mask 209 may include a frame 802 and is configured to seat over a portion of the face of the patient 201. For example, the frame 802 may rest on the ears 804 and nose 806 of the patient 201. In an alternate embodiment, the frame 802 may rest on the cheeks 808. In yet another embodiment, the frame 802 may suspend or extend from a band (not shown) wrapped fully or partially around the head.

The mask 209 may include at least one sensor 206 adapted to seat over a portion of at least one of the extraocular muscles when the mask 209 is positioned on the head of the patient 201. The sensor 206 may be a surface electrode, such as a preamplified electrode. In some embodiments, the sensor 206 may extend from the frame 802 via a bridge 810 to rigidly connect with the frame 802. In another embodiment, the bridge 810 may be an articulable arm that may extend, pivot, flex, and/or rotate to allow the sensor 206 to be adjusted in relation to the face of the patient 201. An example of an articulable arm that may be suitable for some embodiments is the Model No. 96130 arm manufactured by Moffatt Products, Inc. (Watertown, S. Dak.). Use of a preamplified surface electrode as the sensor 206 may enable detection of an evoked response resulting from reduced stimuli intensity relative to passive surface electrodes. The frame 802 may have a perimeter portion 812 disposed in front of the eyes when in use, and may surround glass or plastic lenses or may not include lenses.

In some embodiments, the mask 209 of FIG. 8 may include one or more other sensors, such as accelerometers. These other sensors may be included in the frame 802, in an elastic band, or may be coupled with the mask 209 via one or more wires. These other sensors may provide data useful for normalization and/or feedback, as discussed above.

Figure 9:
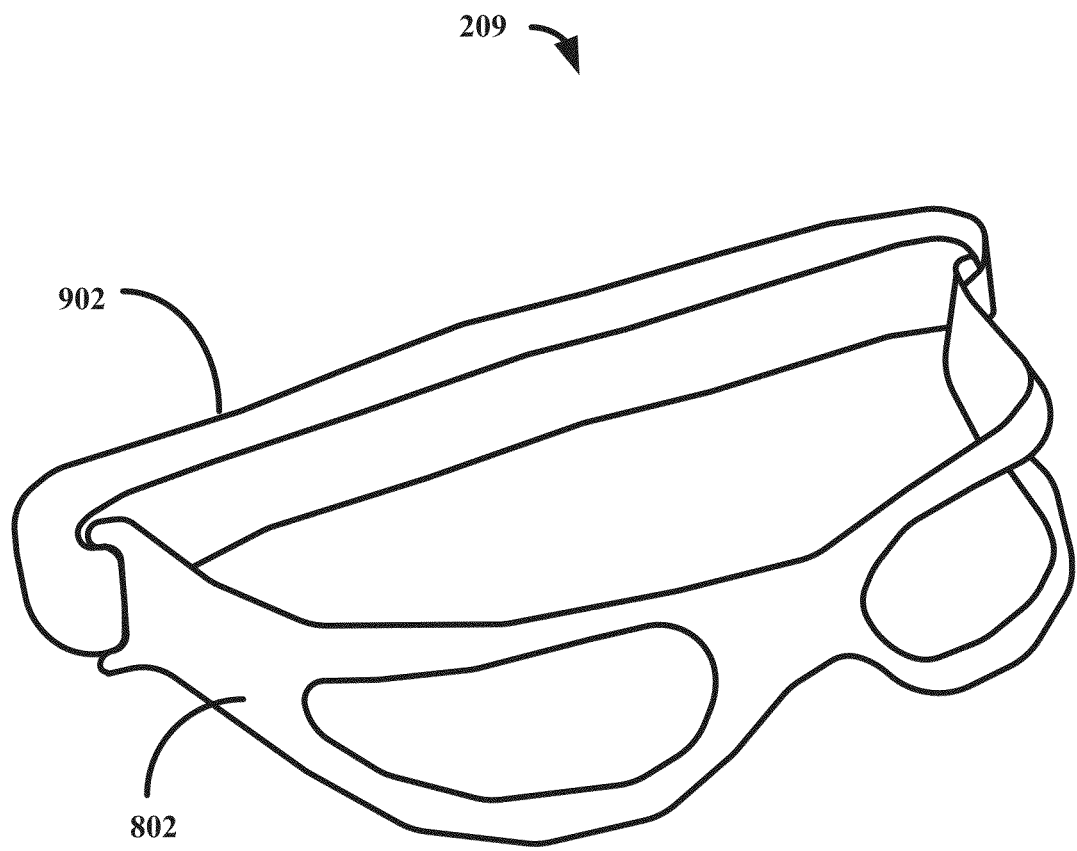
FIG. 9 illustrates an apparatus for measuring oVEMP response, according to various embodiments.

FIG. 9 illustrates another embodiment of a mask 209 for measuring oVEMP response. The mask 209 may include a frame 802 to seat over the nose of the patient. The frame 802 may be connected to a stretchable band 902 adapted to wrap around the head of the patient 201.

As discussed above, some methods and apparatus may provide for consistent and quickly deployable measuring of the cVEMP and/or the oVEMP. To provide for such measurements, some embodiments of an apparatus may provide a resting area for the patient's chin while causing the patient to lean (i.e., tilt or bend) forward. In doing so, the apparatus may cause the patient to flex his or her neck in a manner that causes at least a portion of the sternocleidomastoid muscles to contract without straining the temporomandibular joint and/or neck and spine.

Figure 10A:
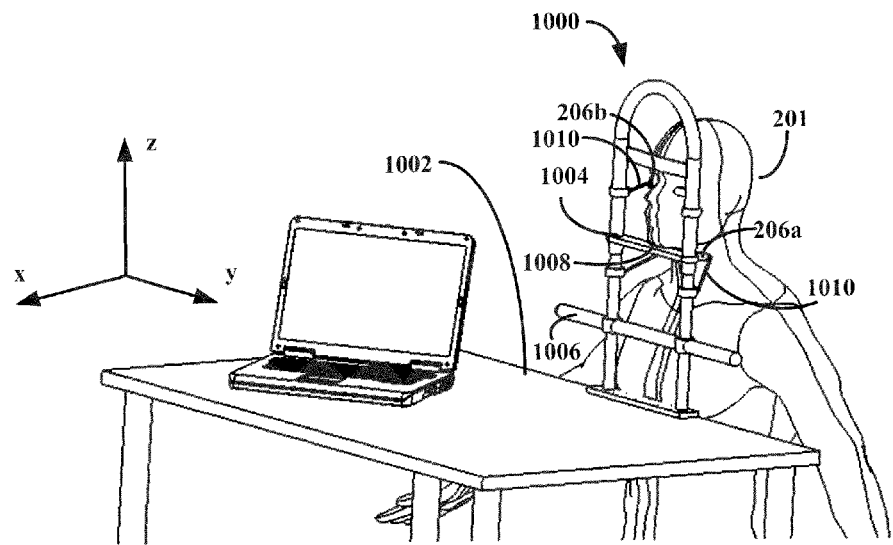
FIGS. 10A-10C illustrate several views of an apparatus for measuring both cervical vestibular evoked myogenic potential (cVEMP) and oVEMP responses, according to various embodiments.
Figure 10B:
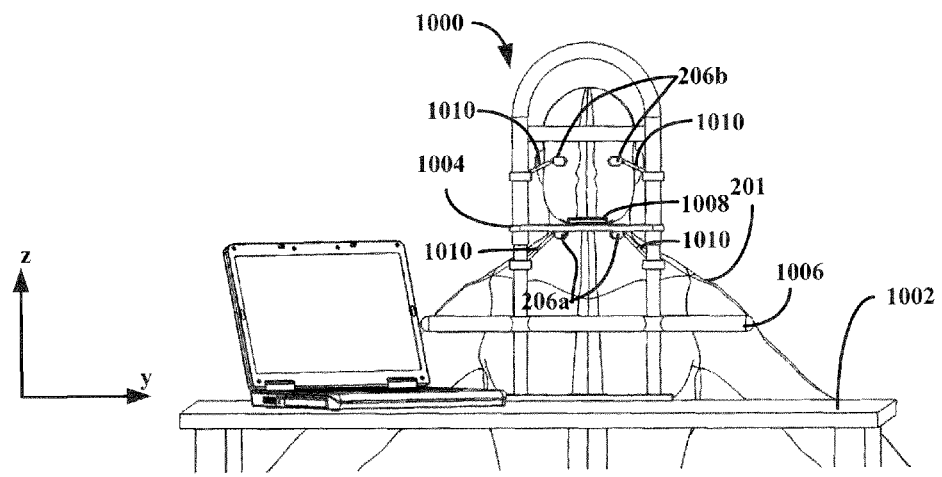
Figure 10C:
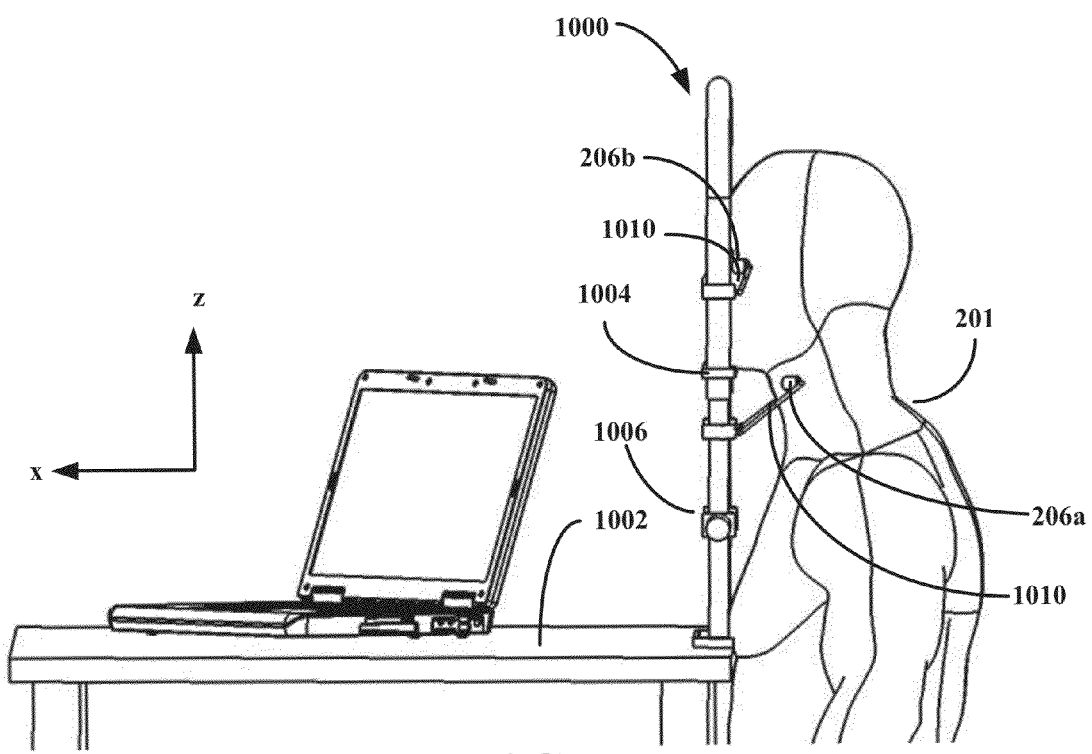

FIGS. 10A-10C illustrate several views of an apparatus 1000 for measuring cVEMP and oVEMP responses, according to various embodiments. Specifically, FIG. 10A shows a perspective view, FIG. 10B shows a front view, and FIG. 10C shows a side view. The apparatus 1000 may be mounted on a table top 1002. The table top 1002 may be motorized to be adjusted to a suitable height (along the z-direction) for the patient 201. An example of a motorized table that may be suitable for some embodiments is Model No. 01-TBL001, manufactured by Woodlyn, Inc. (Arlington Heights, Ill.). The patient 201 may sit or stand proximal to the table top 1002. The apparatus 1000 may include a chin rest 1004, which may be adjustable in the z-direction. In some embodiments, the chin rest 1004 may be adjustable in other directions, including the x-direction and y-direction. The apparatus 1000 may include a handle 1006 as a hand rest. In some embodiments, the apparatus 1000 may be used with existing air-conduction VEMP systems or future to be developed VEMP delivery and recording systems.

The apparatus 1000 may be configured to allow for symmetric neck flexion of the patient 201 against the chin rest 1004. The chin rest 1004 may include a pressure sensor 1008 to measure the pressure (e.g., the force) applied by the patient 201 to the chin rest 1004. The measured pressure may be stored as part of the cVEMP response to normalize the cVEMP measured signal. The measured pressure may also be employed to normalize the cVEMP measured signal. The apparatus 1000 may include a laser guide to provide patterns on a surface or may include a bar with LED lights to which the patient 201 may draw his or her attention for the measurement and/or oVEMP testing. Of course, other guide may be use, such as markings on the wall, etc.

The apparatus 1000 may include articulated arms 1010 to support sensors 206a placed over the sternocleidomastoid muscles for measuring cVEMP responses and/or sensors 206b placed over the inferior oblique muscles for measuring oVEMP responses. The articulated arm 1010 may take the form of any suitable one of the articulated arms described herein. The sensors 206a and 206b may include preamplified surface electromyogram (EMG) electrodes. In some embodiments, a soft band may be applied over sensors 206a to maintain the sensors over the sternocleidomastoid muscle.

Figure 11:
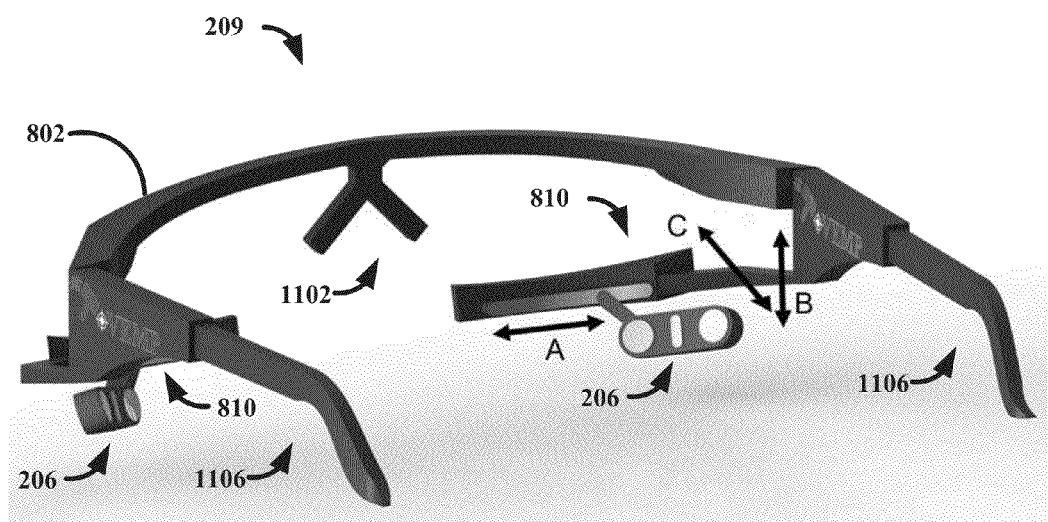
FIG. 11 illustrates an apparatus for measuring patient response, according to various embodiments.

FIG. 11 illustrates another embodiment of a mask 209 for measuring patient response, according to various embodiments. The mask 209 may include a frame 802 and is configured to seat over a portion of the face of the patient 201. In particular, the frame may include a nose rest 1102 to rest on a nose of the patient 201, and ear rests 1106 to rest on the ears of the patient 201.

The mask 209 of FIG. 11 may include at least one sensor 206 adapted to seat over a portion of at least one of the extraocular muscles when the mask 209 is positioned on the head of the patient 201. As illustrated in FIG. 11, the mask 209 may include two sensors 206. Each sensor 206 may be a surface electrode, such as a preamplified electrode, as discussed above. In some embodiments, the sensors 206 may be reusable; in other embodiments, the sensors 206 may be disposable, and may be swapped out and between patients. The sensor 206 may be coupled with the frame 802 via a bridge 810 (e.g., an articulable arm). The bridge 810 may include joints that allow the position of the sensor 206 to be adjusted in the medial to lateral direction (denoted by "A"), the superior to inferior direction (denoted by "B"), and the anterior to posterior direction (denoted by "C") to accommodate the physical characteristics of the patient 201 and adjust the position of the sensors 206 in relation to the face of the patient 201. In some embodiments, a disposable elastic wrap may be provided with the mask 209 to hold the electrodes over the sternocleidomastoid muscles. The disposable elastic wrap may be, for example, a self-adhering cohesive wrap as commonly used in bandaging applications. In some embodiments, the mask 209 of FIG. 11 may include one or more other sensors, such as accelerometers. These other sensors may be included in the frame 802, in an elastic band, or may be coupled with the mask 209 via one or more wires. These other sensors may provide data useful for normalization and/or feedback, as discussed above.

Figure 12A:
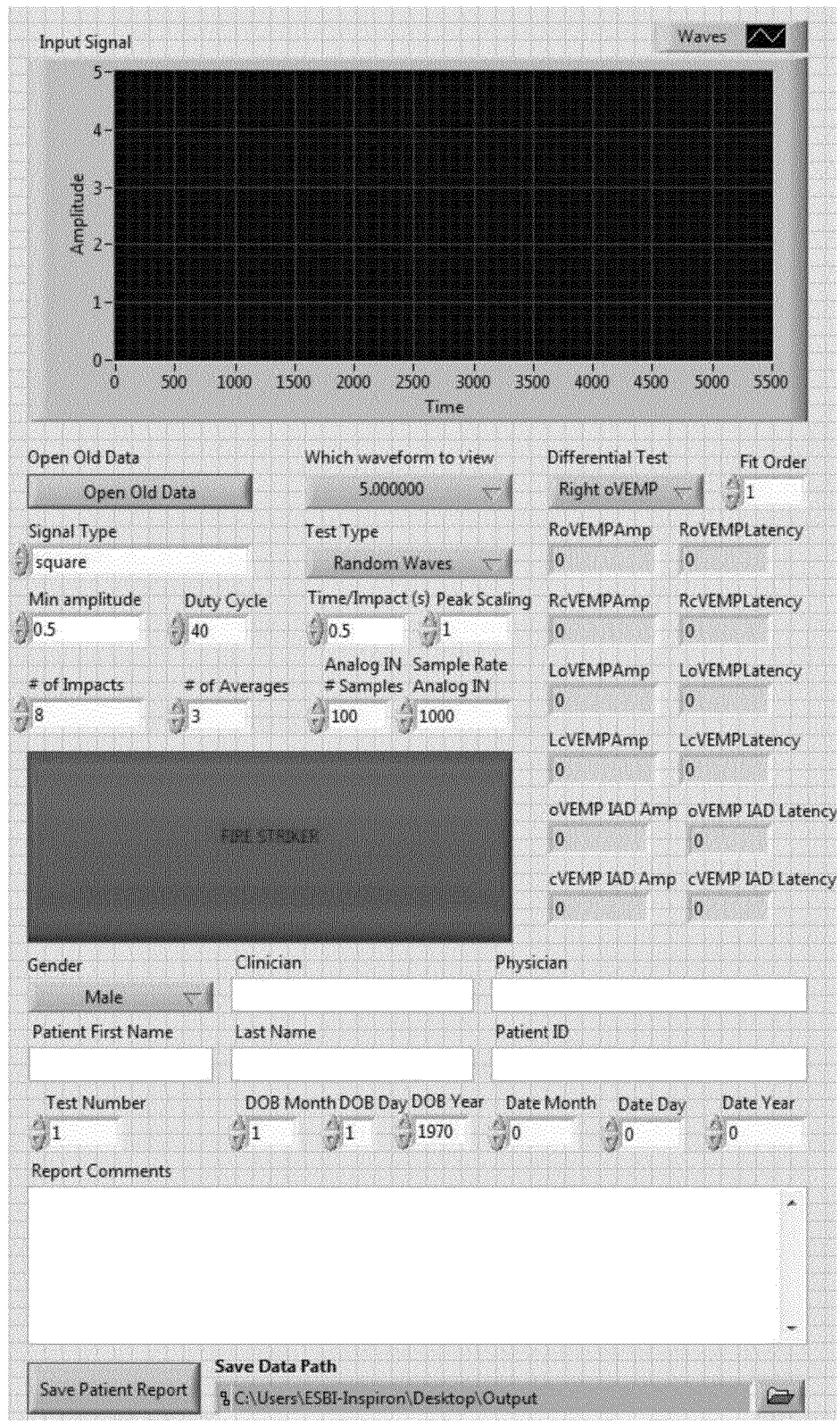
FIGS. 12A-12C illustrate a graphical user interface for viewing patient responses, according to various embodiments.
Figure 12B:
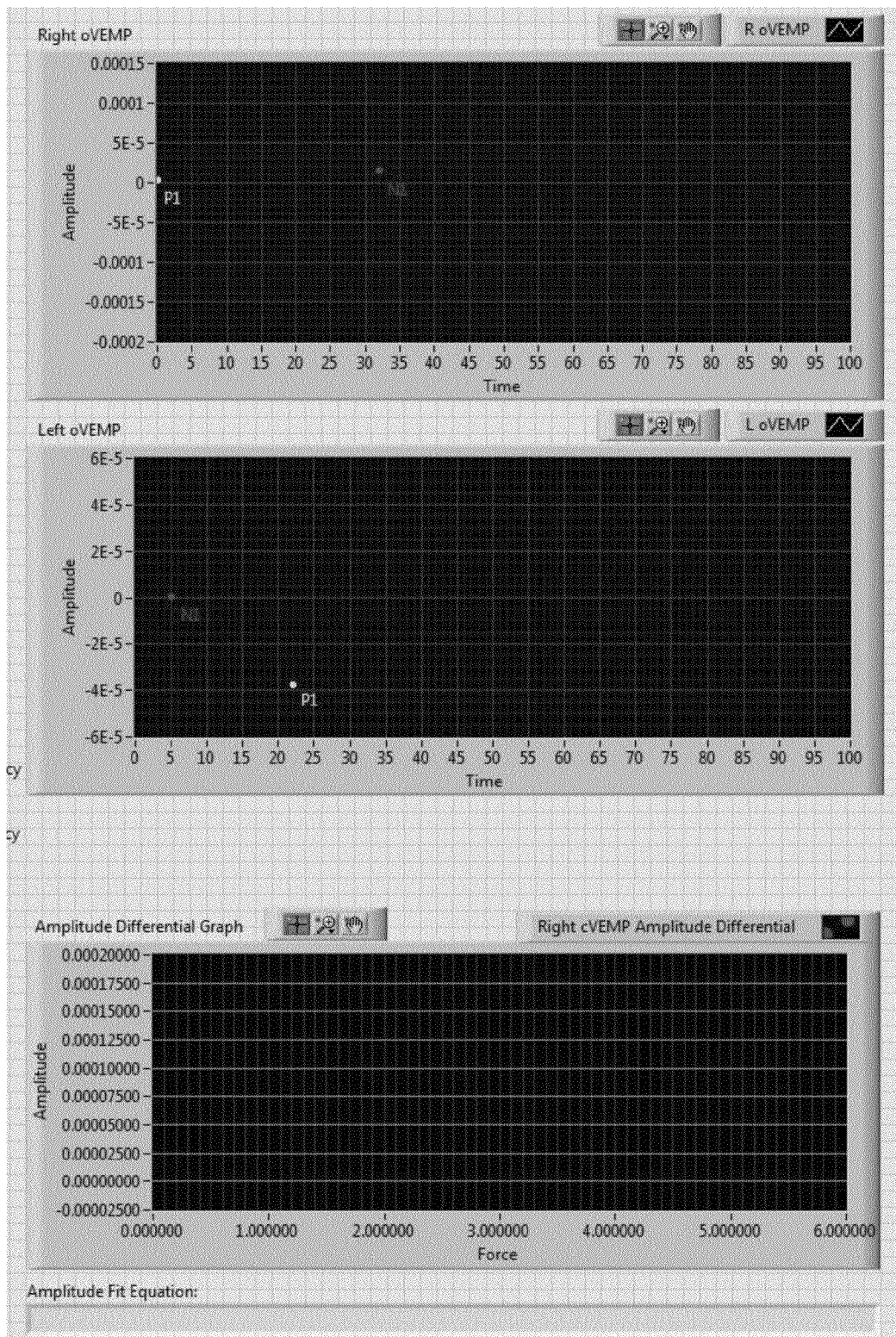
Figure 12C:
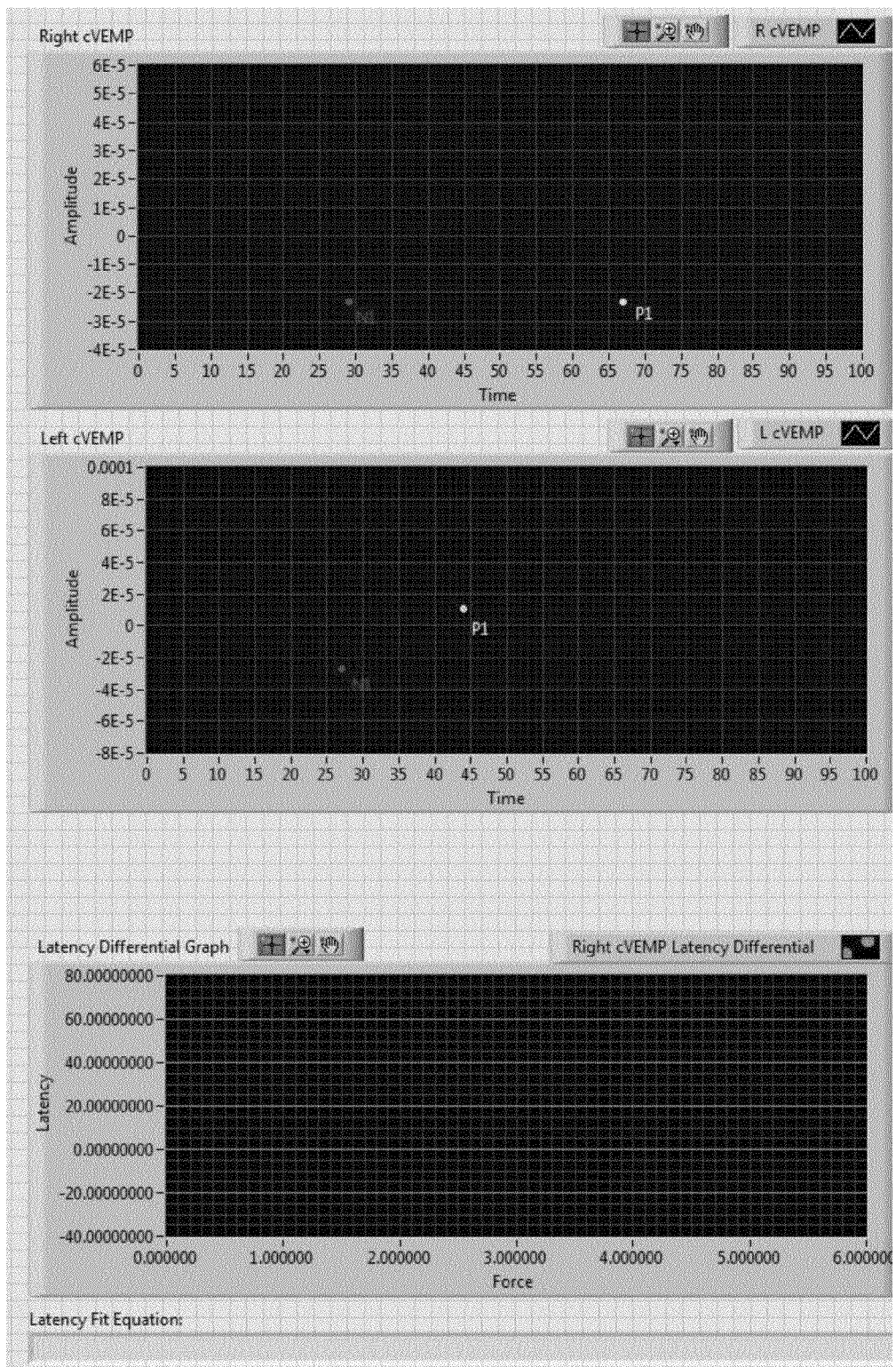

FIGS. 12A-12C illustrate a graphical user interface for viewing patient responses, according to various embodiments. In particular, FIG. 12A depicts a first portion that may be arranged as the left column in a display, FIG. 12B depicts a second portion that may be arranged as the center column in a display, and FIG. 12C depicts a third portion that may be arranged as the right column in a display. The left column may include a display of the amplitude of each strike as a function of time. Drop-down menus below may allow the operator to customize the test parameters used. In particular, the drop-down menus may allow selection of the amplitude of the strike, number of strikes per second, elections regarding the way the data is recorded, analyzed, and displayed, and also the pattern of stimulus delivery. For example, the scaled delivery amplitude can be ascending, descending, or random over a fixed stimulus delivery interval. Alternatively it can be delivered with amplitude that is fixed.

The top four displays in the center and right columns plot the evoked potentials for the right and left cVEMP and oVEMP responses, respectively. The bottom displays in the center and right panel display the amplitude differential and latency differentials so that input-output functions can be measured. In some embodiments, the data may be captured and calculated for right and left cVEMP and oVEMP responses. The first column may include the display of the amplitude of each individual strike as a function of time. In some embodiments, only a subset of the portions of the graphical user interface illustrated in FIGS. 12A-12C may be included in a display together, and others may be accessible by selecting various on-screen options or may not be included at all.

Figures 13A, 13B, 13C:
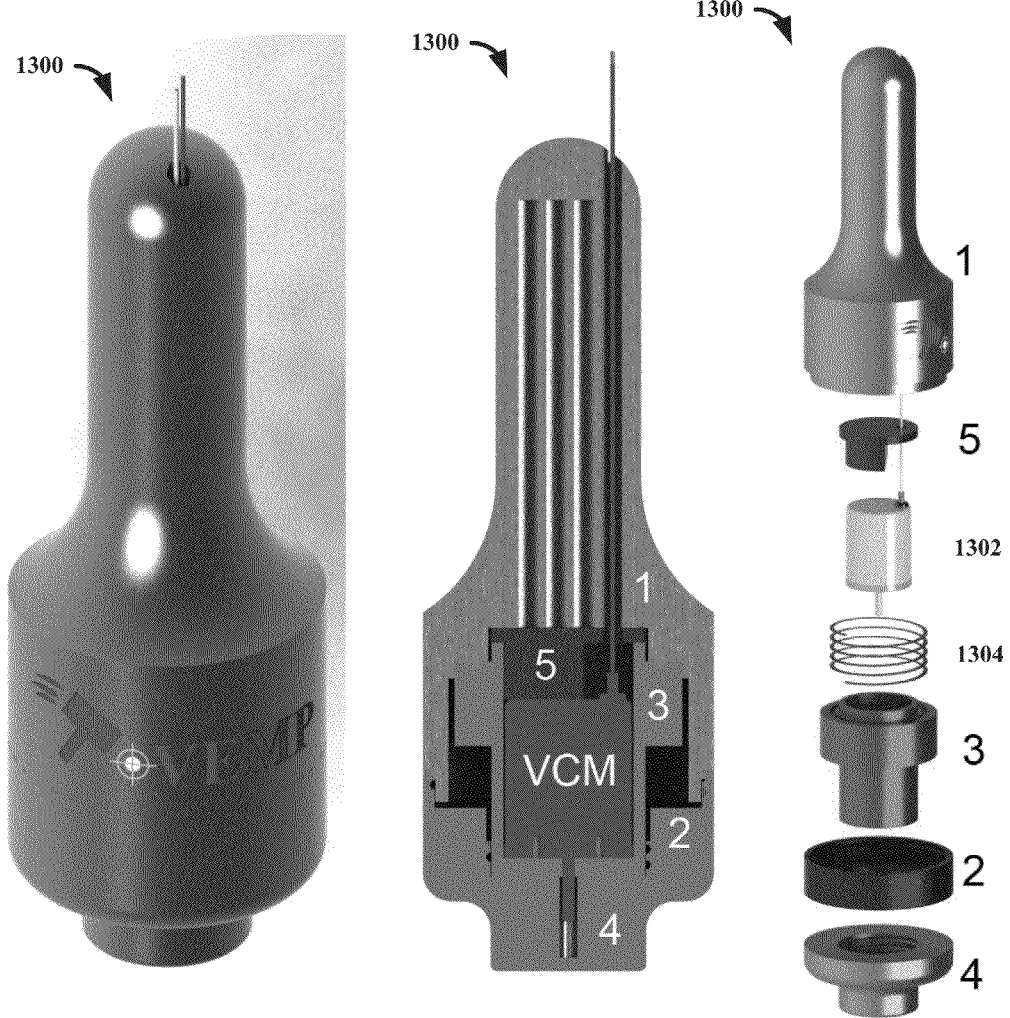
FIGS. 13A-13C illustrate a handheld electrically driven actuator, according to various embodiments.

FIGS. 13A-13C illustrate a handheld electrically driven actuator 1300, according to various embodiments. In particular, FIG. 13A is a perspective view of the handheld electrically driven actuator 1300, FIG. 13B is a cross-sectional view of the handheld electrically driven actuator 1300, and FIG. 13C is an exploded view of the handheld electrically driven actuator 1300. Some or all of the components of the handheld electrically driven actuator 1300 may be formed by 3D printing. As illustrated, Component 1 is the main handpiece, which may be rigidly secured to component 2. This may allow the striking unit to be placed and secured inside of the handpiece during assembly. Note that a custom fabricated single spring may be placed so that when a 1.5 kg load is applied, component 2 is allowed to compress down onto component 4, readying the device to be deployed. The actuator 1302 (e.g., a voice-coil motor) may be rigidly secured in place between components 3 and 5. The striker shaft may impact component 4, which may be rigidly secured to component 3, thereby delivering the bone conduction stimuli to the patient's head when placed at, e.g., the Fz position. A spring 1304, which may be custom manufactured, may create a uniform load before stimulus delivery when compressed.

The embodiments described above are intended to be merely exemplary; numerous variations and modifications will be apparent to those skilled in the art. All such variations and modifications are intended to be within the scope of the present disclosure as defined in any appended claims.

It should be recognized by one of ordinary skill in the art that the foregoing methodology may be performed in a video processing environment and the environment may include one or more processors for processing computer code representative of the foregoing described methodology. The computer code may be embodied on a non-transitory computer readable medium. For example, the computer code may be embodied in a computer program product. Additionally, the functions of the methods discussed herein may be distributed among a plurality of processors (either local or remote from one another).

The systems and methods disclosed herein may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other programmable logic device (PLD)), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, networker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software or a magnetic tape), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL.).

Wireless communication may include a transmission of information as a signal over any portion of the electromagnetic spectrum, including infrared, and radio. The transmission of the information may be part of a wireless network having a defined set of protocol (i.e., IEEE 802.11, Zigbee, WPAN, and Bluetooth).

Various embodiments of the bone conduction systems and techniques disclosed herein may provide a substantial societal benefit by one or more of: lower production costs creating greater opportunity for these systems to be purchased and used by more hospitals, clinics, and clinicians' offices; reducing the test time, allowing more efficient screening for ototoxicity and hospital fall risk as well as allowing the testing of groups that currently cannot tolerate testing such as children, the elderly, and those with conductive hearing loss; more accurate assessment of post-military injury of the inner ear; and more accurate diagnosis of inner ear disorders that produce gravitational receptor dysfunction.

Some embodiments may allow the precision control of bone conduction stimuli necessary to test novel stimulus paradigms, determine the specific evoked potential threshold, determine the maximal utricular or saccular response, and to be able to calculate input-output functions. By contrast, commercially available air-conduction VEMP systems can only determine the event threshold, and because these systems do not have FDA clearance or approval, the manufacturers instruct clinicians not to use their devices for performing VEMP studies clinically.

What is claimed is:
1. An apparatus, comprising:
a housing having a striking end;
an impactor disposed proximal to the striking end, the impactor operatively linked to a guide disposed within the housing, the impactor configured to travel from a starting point and a striking point spaced a predetermined distance away from the starting point, wherein the striking point is disposed between the starting point and a point of maximal extension of the impactor; and an electrically driven actuator system, at least partially enclosed within the housing, the electrically driven actuator system configured to cause the impactor to travel from the starting point to the striking point, thereby delivering a mechanical stimuli for transmission to a skull bone;

wherein the electrically driven actuator system is configured to controllably decelerate the impactor prior to the impactor reaching the striking point.

2. The apparatus of claim 1, wherein the housing is longitudinal and forms a handle at a non-striking end distal to the striking end.

3. The apparatus of claim 1 further comprising:
a first spring disposed in the housing and arranged to store energy when motion of the electrically driven actuator system causes the impactor to travel to the starting point.

4. The apparatus of claim 1, wherein the electrically driven actuator system comprises an electrically driven actuator connected to the impactor through an inertial mass, the inertial mass being suspended between two opposing springs secured to the housing.

5. The apparatus of claim 1, wherein the electrically driven actuator system is configured to accelerate the impactor along a linear guide.

6. The apparatus of claim 1, wherein the electrically driven actuator system is configured to accelerate the impactor along an angular guide.

7. The apparatus of claim 1, wherein:
the electrically driven actuator system is configured to controllably decelerate the impactor prior to the impactor reaching the striking point by loading a spring as the impactor moves toward the striking point from the starting point.

8. The apparatus of claim 1, wherein less than 50 decibels Hearing Level of sound is generated when the impactor delivers the mechanical stimuli.

9. The apparatus of claim 1, wherein the electrically driven actuator system is configured to deliver a plurality of mechanical stimuli for transmission to the skull bone, and the plurality of mechanical stimuli includes at least four in a span of less than one second.

10. The apparatus of claim 1, wherein the electrically driven actuator system comprises an electrically driven actuator within the housing, and the housing is a handheld body.

11. The apparatus of claim 10, wherein the electrically driven actuator system comprises a controller coupled to the electrically driven actuator, and wherein the apparatus further comprises a switch mounted on the handheld body, the switch coupled to the controller and configured to output a trigger signal to the controller to initiate movement of the impactor.

12. The apparatus of claim 10, wherein the electrically driven actuator system comprises a controller coupled to the electrically driven actuator, and wherein the apparatus further comprises a switch that is remote from the housing, communicatively coupled to the controller, and configured to output a trigger signal to the controller to initiate movement of the impactor.

13. The apparatus of claim 1, wherein the electrically driven actuator system comprises a controller coupled to the electrically driven actuator, and wherein the apparatus further comprises a sensor configured to output an electrical signal to the controller when the impactor is proximal to the striking point.

14. The apparatus of claim 13, wherein the electrical signal triggers a recording of an action potential at a patient, the action potential corresponding to gravitation receptors of an inner ear of the patient.

15. The apparatus of claim 1, wherein the electrically driven actuator system comprises a controller coupled to the electrically driven actuator, wherein the electrically driven actuator system is configured to deliver a plurality of mechanical stimuli for transmission to the skull bone, and wherein the controller directs the electrically driven actuator to deliver a plurality of stimuli until a zero-response action potential is measured.

16. The apparatus of claim 1, further comprising:
a frame configured to seat over a portion of a face of the patient; and
a plurality of sensing members, each member comprising at least one electrode fixably attached to an arm extending from the frame, the electrode configured to seat over a portion of extraocular muscles, including a portion of an inferior oblique eye muscle, to detect an action potential thereon.

17. The apparatus of claim 16, wherein the frame forms a pre-defined gap with the extraocular muscles and a globe of the eye so to not exert a pressure thereon.

18. The apparatus of claim 16, wherein the arm is adapted to articulate and adjustably position the electrode to contact skin over the extraocular muscles.

19. The apparatus of claim 16, wherein the electrode is a preamplified electrode.

20. The apparatus of claim 1, further comprising:
an upright structural member;
a vertically adjustable chin rest fixably mounted to the upright structural member, the chin rest being positioned below a position that causes a patient to lean in and flex his or her neck in such a manner that causes a portion of sternocleidomastoid muscles of the patient to contract;
a sensor extending from the upright structural member to seat over the portion of the sternocleidomastoid muscles; and
a sensor extending from the upright structural member to seat over the portion of the inferior oblique muscles.

* * * * *